United States Patent [19]
Manzo et al.

[11] Patent Number: 6,024,748
[45] Date of Patent: Feb. 15, 2000

[54] SINGLESHOT ANASTOMOSIS INSTRUMENT WITH DETACHABLE LOADING UNIT AND METHOD

[75] Inventors: Scott E. Manzo, Shelton; Richard D. Gresham, Monroe; Kevin Sniffin, Danbury; Peter W.J. Hinchliffe, New Haven, all of Conn.

[73] Assignee: United States Surgical Corporation, Norwalk, Conn.

[21] Appl. No.: 08/877,701

[22] Filed: Jun. 17, 1997

Related U.S. Application Data

[63] Continuation-in-part of application No. 08/685,385, Jul. 23, 1996, Pat. No. 5,707,380.

[51] Int. Cl.$^7$ ................................................ A61B 17/04
[52] U.S. Cl. ............................ 606/153; 206/340; 227/19
[58] Field of Search ................................... 606/153, 142, 606/143; 227/61, 19; 206/340

[56] References Cited

U.S. PATENT DOCUMENTS

| | | |
|---|---|---|
| D. 276,650 | 12/1984 | Green et al. |
| 2,968,041 | 1/1961 | Skold |
| 3,152,336 | 10/1964 | Brady |
| 3,232,089 | 2/1966 | Samuels et al. |
| 3,366,301 | 1/1968 | Mallina |
| 3,519,187 | 7/1970 | Kapitanov et al. |
| 3,575,038 | 4/1971 | Mallett |
| 3,856,016 | 12/1974 | Davis |
| 3,908,662 | 9/1975 | Razgulov et al. |
| 3,954,108 | 5/1976 | Davis |
| 4,152,920 | 5/1979 | Green |
| 4,166,466 | 9/1979 | Jarvik |
| 4,201,314 | 5/1980 | Sammuels et al. |
| 4,226,242 | 10/1980 | Jarvik |

(List continued on next page.)

FOREIGN PATENT DOCUMENTS

| | | |
|---|---|---|
| 0 384 647 | 2/1990 | European Pat. Off. |
| 0 594 004 A1 | 4/1994 | European Pat. Off. |
| 0 656 191 A2 | 6/1995 | European Pat. Off. |
| 935490 | 8/1963 | United Kingdom |
| WO 88/01486 | 3/1988 | WIPO |
| WO 95/15715 | 6/1995 | WIPO |
| WO 95/35065 | 12/1995 | WIPO |

OTHER PUBLICATIONS

Information Booklet for: LIGACLIP * Ligating Clips, Appliers & Removers * For security in Ligation Ethicon, Inc., 1982.

Information Booklet for: Deep Surgery Advantage—Dramatic New Access Plus Automatic–Feed in Vessel Ligation, Hemoclip® automatic ligating clip system, Edward Weck & Company, Inc., Sep. 1996.

Information Booklet for: Auto Suture® Premium Surgiclip™ Titanium disposable automatic clip appliers, United States Surgical Corporation, 1981.

*Primary Examiner*—Gary Jackson

[57] ABSTRACT

There is disclosed a surgical instrument and loading unit for performing an anastomosis of first and second blood vessels. The surgical instrument includes a handle assembly and a body portion extending distally from the handle assembly. The detachable loading unit includes an anvil releasably engagable with a distal end of the body portion and having a plurality of fasteners disposed in channels about the circumference of a distal end of the anvil. A pusher is slidably mounted over the anvil such that distal movement of the pusher in response to actuation of the handle assembly cams the fasteners between the anvil and a distal end of the pusher to simultaneously crimp the fasteners about tissue. A method of performing an anastomosis is also disclosed and includes positioning a first vessel in the loading unit and partially inserting the first vessel through an opening in a second vessel. The surgical instrument is subsequently attached to the loading unit and the handle assembly is actuated to crimp fasteners about the first and second vessels to form an anastomosis.

30 Claims, 22 Drawing Sheets

U.S. PATENT DOCUMENTS

| | | |
|---|---|---|
| 4,242,902 | 1/1981 | Green . |
| 4,299,224 | 11/1981 | Noiles . |
| 4,316,468 | 2/1982 | Klieman et al. . |
| 4,325,376 | 4/1982 | Klieman et al. . |
| 4,350,160 | 9/1982 | Kolesov et al. . |
| 4,368,736 | 1/1983 | Kaster . |
| 4,372,316 | 2/1983 | Blake, III et al. . |
| 4,408,603 | 10/1983 | Blake, III et al. . |
| 4,412,539 | 11/1983 | Jarvik . |
| 4,425,915 | 1/1984 | Ivanov . |
| 4,430,997 | 2/1984 | DiGiovanni et al. . |
| 4,432,925 | 2/1984 | Blake, III . |
| 4,452,376 | 6/1984 | Klieman et al. . |
| 4,466,436 | 8/1984 | Lee . |
| 4,480,640 | 11/1984 | Becht . |
| 4,509,518 | 4/1985 | McGarry et al. . |
| 4,522,207 | 6/1985 | Klieman et al. . |
| 4,534,351 | 8/1985 | Rothfuss et al. . |
| 4,586,503 | 5/1986 | Kirsch . |
| 4,598,711 | 7/1986 | Deniega . |
| 4,611,595 | 9/1986 | Klieman et al. . |
| 4,616,650 | 10/1986 | Green et al. . |
| 4,700,703 | 10/1987 | Resnick et al. . |
| 4,712,549 | 12/1987 | Peters et al. . |
| 4,733,664 | 3/1988 | Kirsch et al. . |
| 4,759,364 | 7/1988 | Boebel . |
| 4,809,695 | 3/1989 | Gwathmey et al. . |
| 4,821,939 | 4/1989 | Green . |
| 4,872,874 | 10/1989 | Taheri . |
| 4,929,240 | 5/1990 | Kirsch et al. . |
| 4,930,674 | 6/1990 | Barak . |
| 4,979,954 | 12/1990 | Gwathmey et al. . |
| 4,983,176 | 1/1991 | Cushman et al. . |
| 5,025,779 | 6/1991 | Bugge . |
| 5,030,226 | 7/1991 | Green et al. . |
| 5,104,395 | 4/1992 | Thornton et al. . |
| 5,112,343 | 5/1992 | Thornton . |
| 5,122,150 | 6/1992 | Puig et al. . |
| 5,188,638 | 2/1993 | Tzakis . |
| 5,192,288 | 3/1993 | Thompson et al. . |
| 5,234,447 | 8/1993 | Kaster et al. . |
| 5,314,436 | 5/1994 | Wilk . |
| 5,340,360 | 8/1994 | Stefanchik . |
| 5,346,115 | 9/1994 | Perouse et al. . |
| 5,354,304 | 10/1994 | Allen et al. . |
| 5,366,462 | 11/1994 | Kaster et al. . |
| 5,403,333 | 4/1995 | Kaster et al. . |
| 5,431,668 | 7/1995 | Burbank, III et al. . |
| 5,443,198 | 8/1995 | Viola et al. . |
| 5,486,187 | 1/1996 | Schenck . |
| 5,501,698 | 3/1996 | Roth et al. . |
| 5,503,617 | 4/1996 | Jako . |

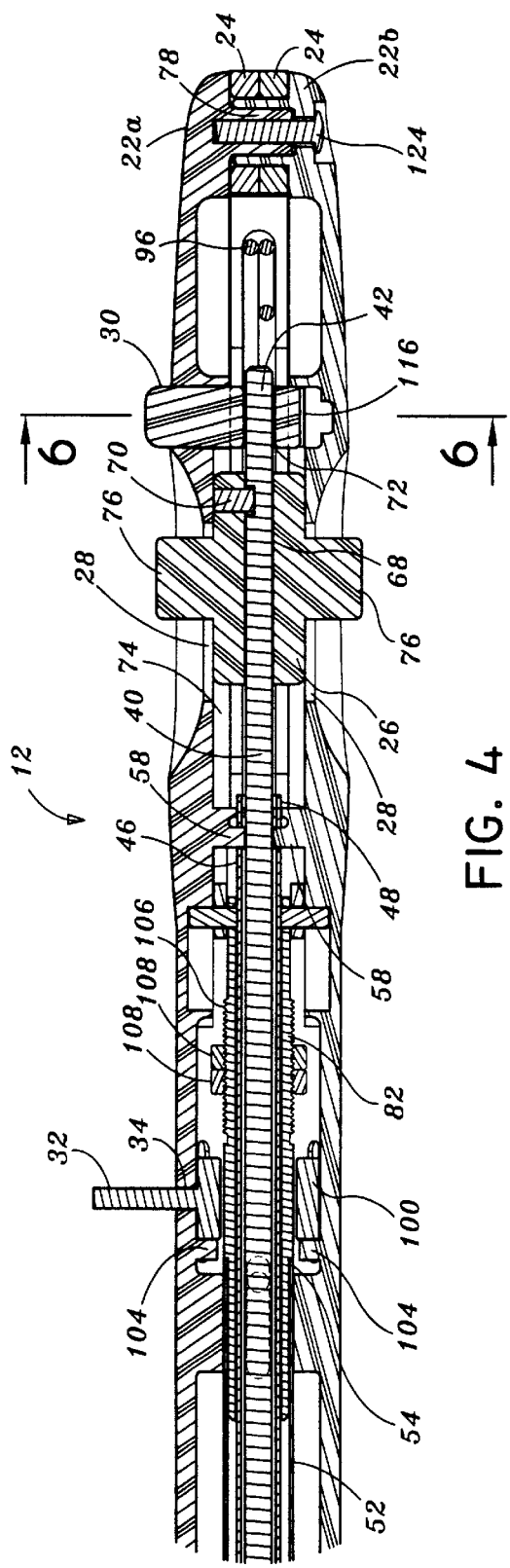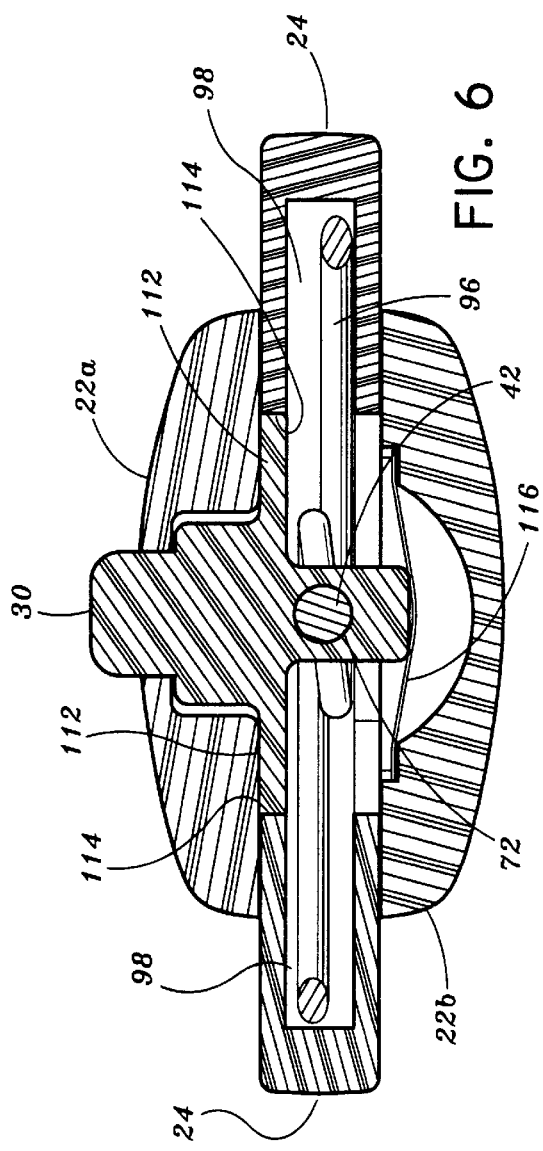
FIG. 4
FIG. 6

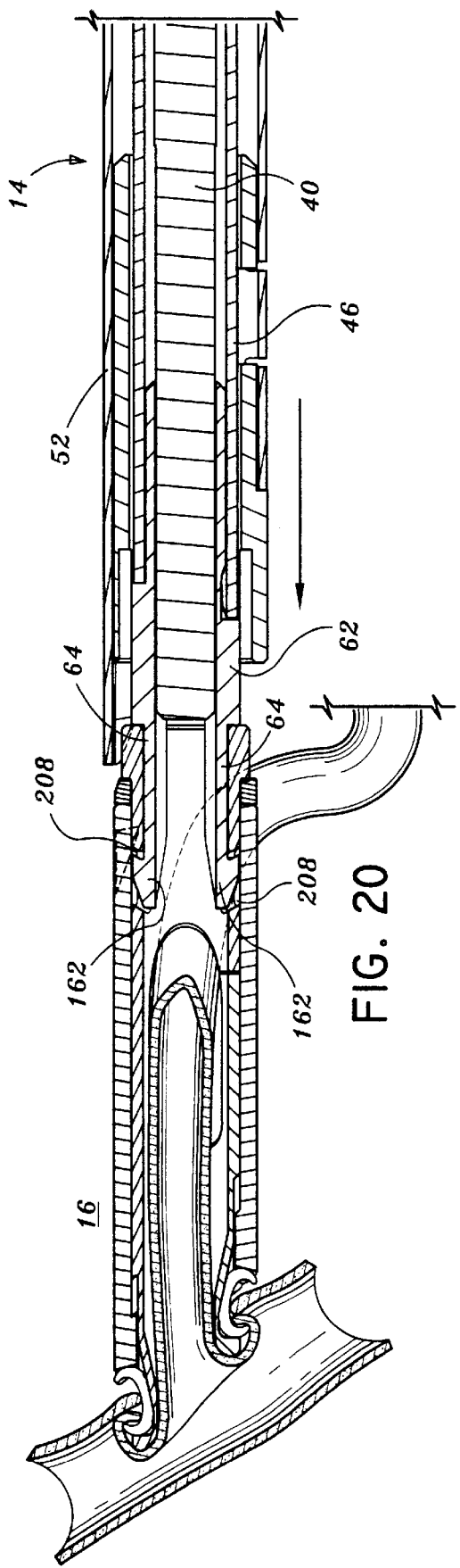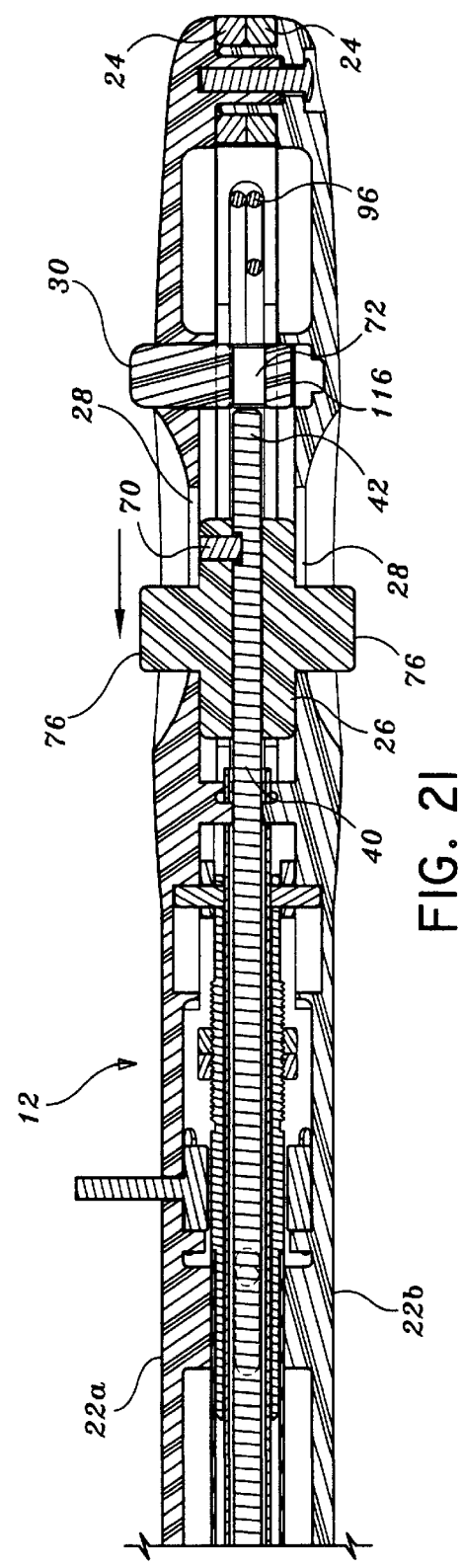

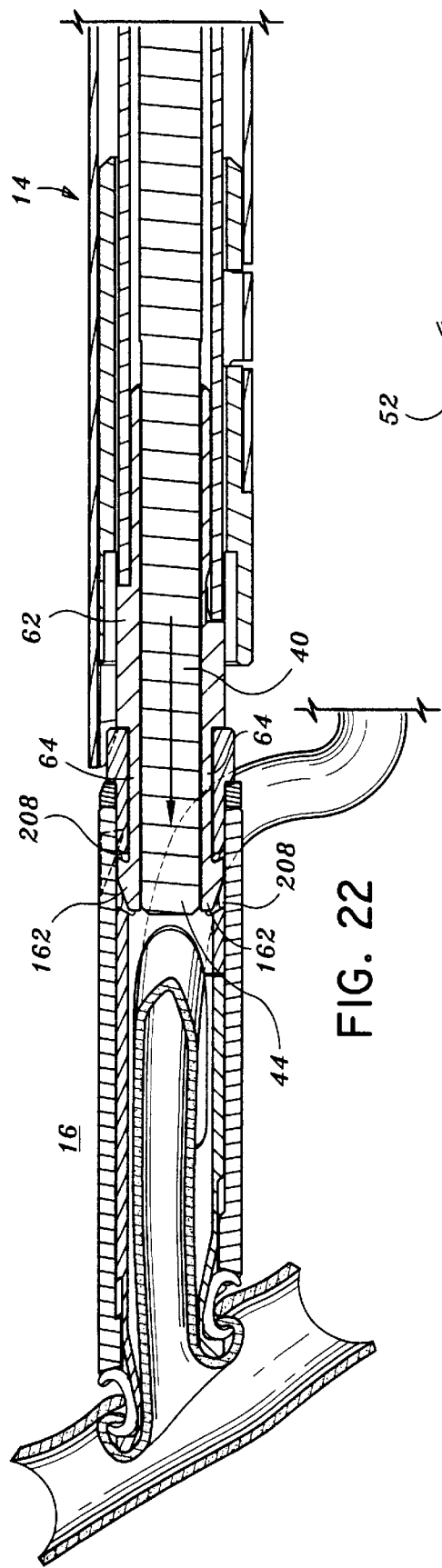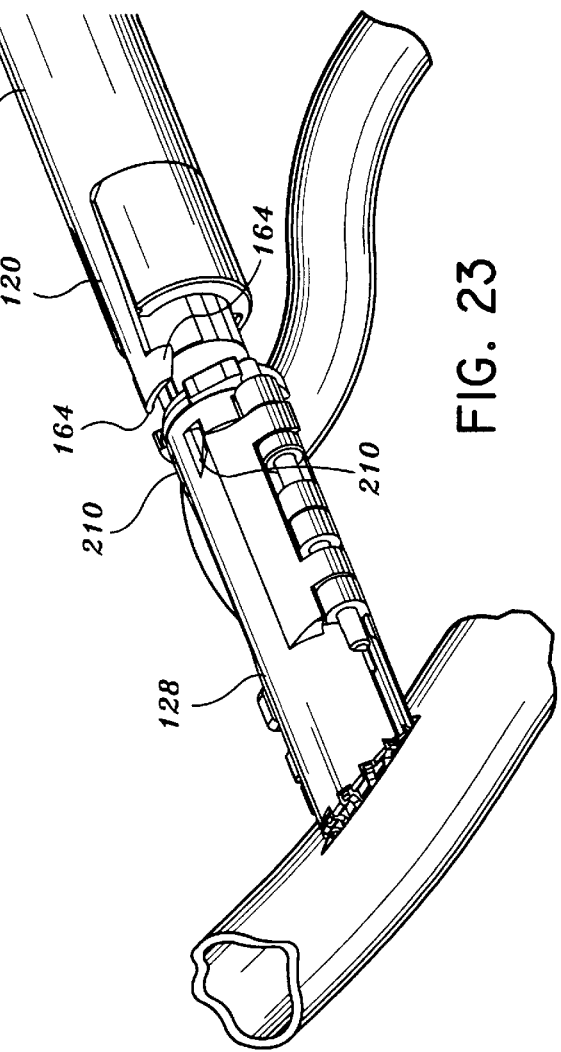
FIG. 22
FIG. 23

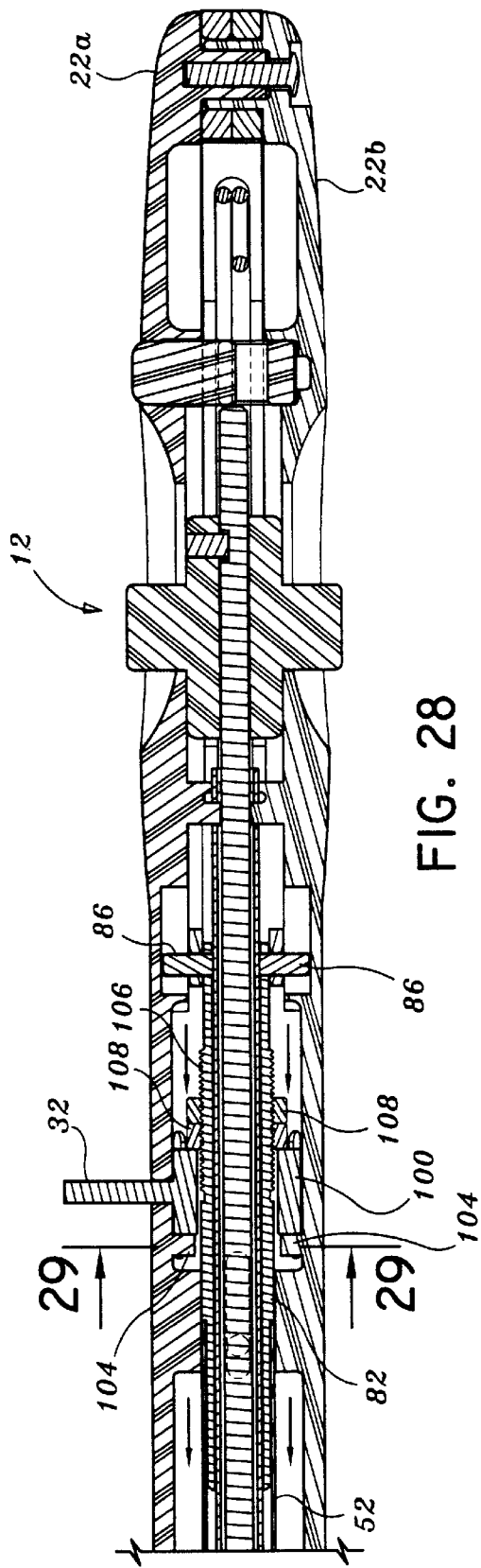
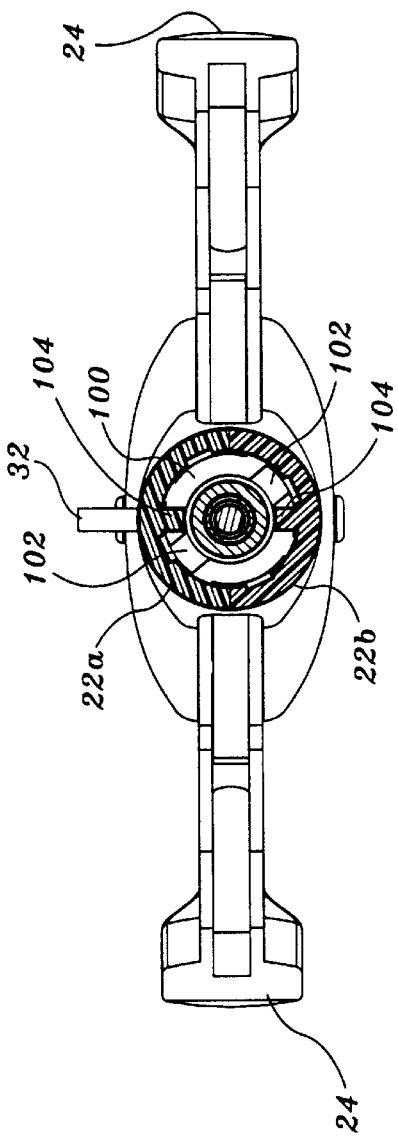
FIG. 28
FIG. 29

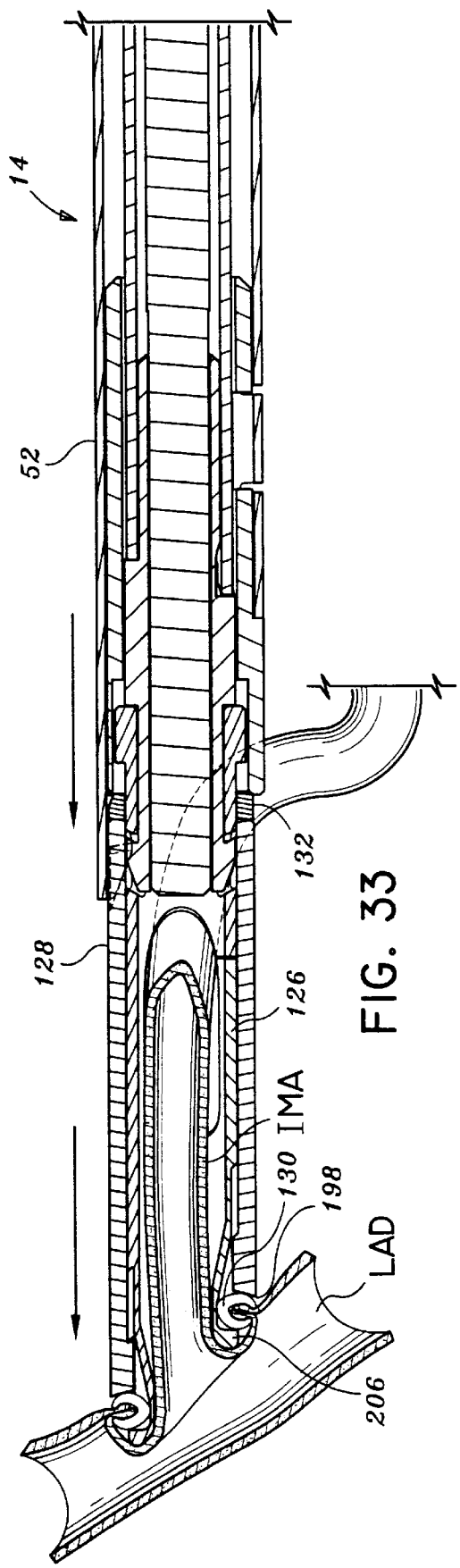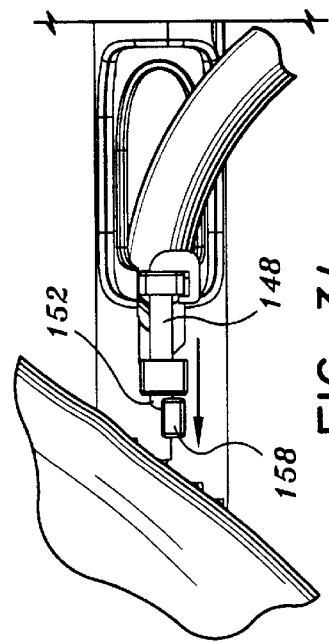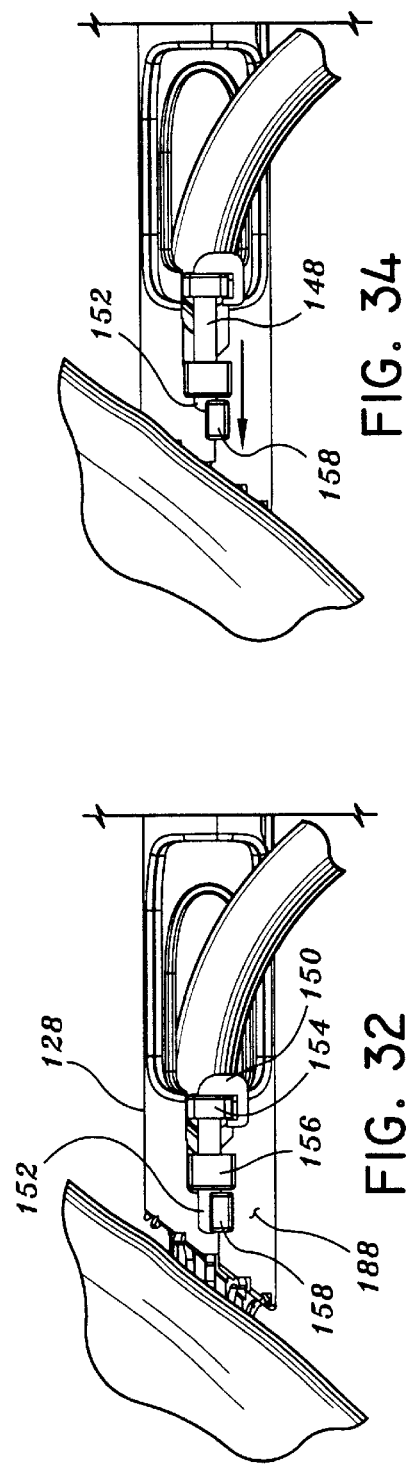
FIG. 33
FIG. 34
FIG. 32

SINGLESHOT ANASTOMOSIS INSTRUMENT WITH DETACHABLE LOADING UNIT AND METHOD

CROSS-REFERENCE TO RELATED APPLICATION

This application is a continuation-in-part of U.S. patent application Ser. No. 08/685,385, filed Jul. 23, 1996, U.S. Pat. No. 5,707,380 entitled "Anastomosis Instrument and Method", the disclosure of which is incorporated by reference herein.

BACKGROUND

1. Technical Field

The subject disclosure relates to a surgical apparatus having a detachable loading unit and method for performing anastomosis of tubular body structures, and more particularly to an instrument for joining vascular tissue.

2. Background of Related Art

Coronary artery disease is often characterized by lesions or occlusions in the coronary arteries which may result in inadequate blood flow to the myocardium, or myocardial ischemia, which is typically responsible for such complications as angina pectoris, necrosis of cardiac tissue (myocardial infarction), and sudden death. In some cases, coronary artery disease may be treated by the use of drugs and by modifications in behavior and diet. In other cases, dilatation of coronary arteries may be achieved by such procedures as angioplasty, laser ablation, atherectomy, catheterization, and intravascular stents.

For certain patients, coronary artery bypass grafting (CABG) is the preferred form of treatment to relieve symptoms and often increase life expectancy. CABG consists of direct anastomosis of a vessel segment to one or more of the coronary arteries. For example, a reversed segment of the saphenous vein may be grafted at one end to the ascending aorta as an arterial blood source and at the other end to a coronary artery at a point beyond the arterial occlusion. Alternatively, the internal mammary artery (IMA) is located in the thoracic cavity adjacent the sternum and is likewise suitable for grafting to a coronary artery, such as the left anterior descending artery (LAD).

The performance of CABG typically requires access to the heart, blood vessels and associated tissue. Access to the patient's thoracic cavity may be achieved in an open procedure by making a large longitudinal incision in the chest. This procedure, referred to as a median sternotomy, requires a saw or other cutting instrument to cut the sternum and allow two opposing halves of the rib cages to be spread apart. U.S. Pat. No. 5,025,779 to Bugge discloses a retractor which is designed to grip opposite sternum halves and spread the thoracic cavity apart. The large opening which is created by this technique enables the surgeon to directly visualize the surgical site and perform procedures on the affected organs. However, such procedures that involve large incisions and substantial displacement of the rib cage are often traumatic to the patient with significant attendant risks. The recovery period may be extensive and is often painful. Furthermore, patients for whom coronary surgery is indicated may need to forego such surgery due to the risks involved with gaining access to the heart.

U.S. Pat. No. 5,503,617 to Jako discloses a retractor configured to be held by the surgeon for use in vascular or cardiac surgery to retract and hold ribs apart to allow access to the heart or a lung through an operating window. The retractor includes a rigid frame and a translation frame slidably connected to the rigid frame. Lower and upper blades are rotatably mounted to the rigid frame and the translation frame respectively. The window approach enables the surgeon to gain access through a smaller incision and with less displacement of the ribs, and consequently, less trauma to the patient.

Once access to the thoracic cavity has been achieved, surgery on the heart may be performed. Such procedures typically require that the heart beat be arrested while maintaining circulation throughout the rest of the body. Cardioplegic fluid, such as potassium chloride (KC1) is delivered to the blood vessels of the heart to paralyze the myocardium. As disclosed in WO 95/15715 to Sterman et al. for example, cardioplegic fluid is infused into the myocardium through the coronary arteries by a catheter inserted into the ascending aorta. Alternatively, cardioplegic fluid is infused through the coronary veins in a retrograde manner by a catheter positioned in the interior jugular vein accessed at the patient's neck. Such procedures require the introduction of multiple catheters into the blood vessels adjacent the heart, which is complicated procedure requiring that the desired vessels be properly located and accessed. The progression of the guide wires and catheters must be closely monitored to determine proper placement. Furthermore, the introduction of catheters forms punctures in the blood vessels that must be subsequently closed, and there is an increased risk of trauma to the interior walls of the vessels in which the catheters must pass.

Alternatively, the CABG procedure may be performed while the heart is permitted to beat. A surgical instrument is used to stabilize the heart and restrict blood flow through the coronary artery during the graft procedure. Special care must be given to procedures performed on a beating heart, e.g. synchronizing procedures to occur at certain stages in the cardiac cycle, such as between heartbeats.

To perform the CABG procedure, the harvested vessel segment, such as the IMA, is grafted to the coronary artery by end-to-side anastomosis. Typically, sutures are used to graft the vessel segments. However, conventional suturing is complicated by the use of minimally invasive procedures, such as the window approach. Limited access and reduced visibility may impede the surgeon's ability to manually apply sutures to a graft. Additionally, it is difficult and time consuming to manually suture if the CABG procedure is being performed while the heart is beating as the suturing must be synchronized with the heart beat.

The process of manually suturing the harvested vessel segment to a coronary artery is time consuming and requires a great deal of skill on the part of the surgeon. The resulting sutured anastomosis will also be dependent on the skills of the surgeon. In minimally invasive procedures, the ability to suture is even more complicated due to limited maneuverability and reduced visibility. Therefore, a need exists for an apparatus and a procedure that enables the remote anastomosis without piercing the vessels during both conventional and minimally invasive procedures in a consistent and rapid manner. It would be advantageous to provide an apparatus and method having a loading unit containing atraumatic surgical clips for easily manipulating and positioning a pair of vessels for anastomosis.

SUMMARY

There is provided a surgical instrument and a detachable loading unit containing surgical clips for forming an anastomosis between two tubular tissue sections, such as a first and second blood vessel. The detachable loading unit generally includes a fastener support or elongated cylindrical anvil having a plurality of atraumatic clips disposed in slots arranged circumferentially around the outside surface of the distal end of the anvil. A fastener camming member or pusher is provided surrounding the anvil and is slidable with respect to the anvil to deform the clips. Preferably the clips are held within the slots in the anvil by frictional engagement with the pusher. Together, the pusher and the anvil define a passage for receipt of a tubular tissue section, for example, internal mammary artery (IMA). A disk is provided adjacent a proximal end of the anvil to bias the pusher towards the clips to retain the clips against the anvil. Preferably, the anvil and pusher are each formed as complementary halves which are pivoted together about a common pivot point. By separating the halves after the formation of anastomosis, the IMA may easily be removed from the loading unit. A latch mechanism may be provided to retain the halves of the anvil and pusher together until the anastomosis has been performed.

There is also disclosed a surgical instrument which includes a handle assembly having an anvil support or central tube extending distally from the handle assembly. The central tube is fixed with respect to the handle assembly. A pusher tube is slidably mounted over the central tube and is configured to engage the pusher at the distal end of the pusher tube. Actuation of a handle pivotally attached to the handle assembly moves pusher tube distally to drive the pusher against the clips and to form the clips against the anvil.

Preferably, a center rod is provided and is slidably mounted within an interior bore of the central tube. The center rod is actuable from the handle assembly to advance the center rod into a position forcing flexible arms on the central tube into engagement with the anvil to fixedly lock the anvil to the central tube. A handle lockout button may be provided on the handle assembly to block movement of the handles, and therefore prevent actuation of the instrument, until such time as the DLU has been securely locked to the instrument by movement of the center rod.

Further, the surgical instrument may be provided with a release mechanism for remotely opening the halves of the anvil and pusher after anastomosis has been performed.

There is also disclosed a method for forming an anastomosis between first and second blood vessels which includes inserting a first blood vessel within the detachable loading unit and everting an end of the blood vessel about the anvil and at least one leg of each of the clips positioned on the anvil. The DLU with the first blood vessel positioned thereon can then easily be manipulated into an incision formed in a second blood vessel. Once the DLU and everted blood vessel have been positioned within the second blood vessel, the surgical instrument may be attached to the DLU and actuated to crimp the clips about the first and second blood vessels. Subsequently, the DLU can be remotely actuated from the surgical instrument to separate the halves of the anvil and pusher and release the first blood vessel from the DLU. The pusher tube can be withdrawn and disengaged from the pusher and the center rod can be retracted to release the anvil from the instrument. Subsequently, a second fully loaded DLU may be installed on the instrument or, alternatively, the DLU may be disassembled and a next plurality of clips positioned and secured within the slots for subsequent anastomosis.

BRIEF DESCRIPTION OF THE DRAWINGS

Various embodiments are described herein with reference to the drawings wherein:

FIG. 4 is a sectional view of the proximal end of the surgical suturing apparatus;

FIG. 5 is a perspective view of a housing half and a trigger lock button;

FIG. 6 is a sectional view taken along line 6—6 of FIG. 4 and illustrating the handle lock button engaged with the handles;

FIG. 20 is a sectional view of the distal end of the surgical instrument being secured to the proximal end of the detachable loading unit;

FIG. 21 is a sectional view of the handle assembly illustrating a lock slider advancing a center rod distally;

FIG. 22 is a sectional view of the detachable loading unit and distal end of the surgical instrument with the center rod advanced distally to secure the surgical instrument to the detachable loading unit;

FIG. 23 is a perspective view of the detachable loading unit installed on the distal end of the surgical instrument and in a position to secure the harvested vessel to the coronary artery;

FIG. 28 is a sectional view of the handle assembly illustrating the pusher tube being driven distally;

FIG. 29 is a cross-sectional view taken along line 29—29 of FIG. 28 and illustrating the collar lever out of alignment with projections in the handle housing;

FIG. 32 is a perspective view of the detachable loading unit illustrating the latch mechanism in a fully engaged condition holding halves of the detachable loading unit together;

FIG. 33 is a sectional view of the distal end of the surgical instrument illustrating advancement of the pusher tube to drive the pusher of the detachable loading unit distally and crimp the surgical clips about the vessels;

FIG. 34 is a view similar to FIG. 32 with the latch mechanism in a condition immediately prior to being disengaged;

DETAILED DESCRIPTION OF THE PREFERRED EMBODIMENTS

Preferred embodiments of the apparatus and method disclosed herein will be discussed in terms of minimally invasive vascular grafts to the coronary artery. However, the subject apparatus may also find use in performing anastomosis of other tubular or luminal body structures.

Figure 1:
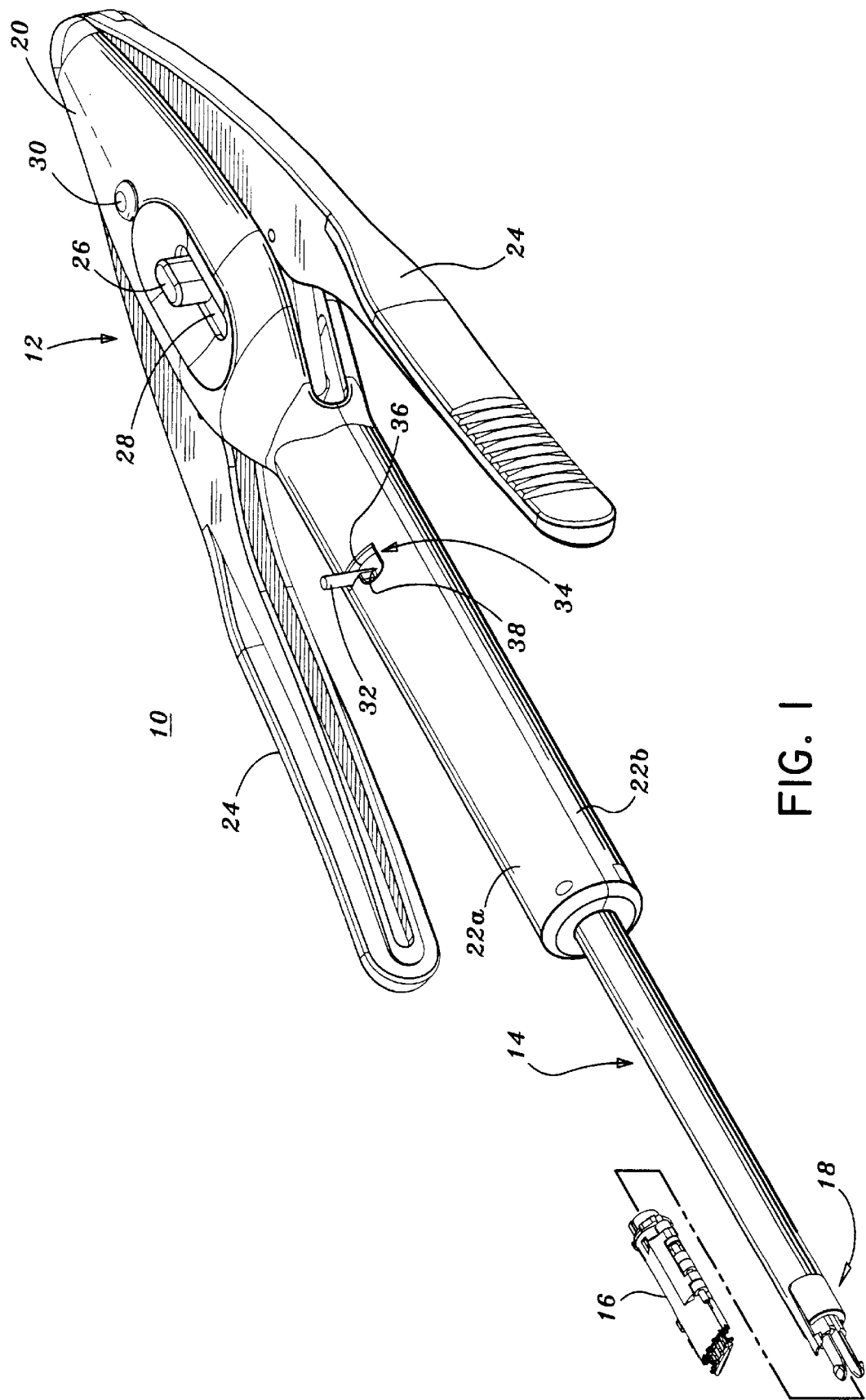
FIG. 1 is a perspective view of a surgical instrument and detachable loading unit in accordance with a preferred embodiment of the present disclosure.

Referring now to the drawings in which like reference numerals identify similar identical elements throughout the various views, and initially to FIG. 1, there is illustrated a surgical instrument 10 having a handle assembly 12 and an elongated tubular body portion 14 extending distally from handle assembly 12. As used herein, the term "proximal" as is traditional refers to that end of the apparatus, or component thereof, which is closer to the operator, while the term "distal" will refer to that end of the apparatus, or component thereof, which is further from the operator. A detachable loading unit 16 is releasably engagable with a distal end 18 of body portion 14. Surgical instrument 10 is provided with body portion 14 which is configured and dimensioned to be inserted through a cannula placed between the ribs. A thorascope (not shown) may be likewise inserted through a second cannula in order to illuminate and visualize the procedure. It should be noted that use of the afore-described instruments and other procedures is also contemplated.

Surgical instrument 10 is configured to receive a harvested vessel e.g. the internal mammary artery (IMA), through a passage in the detachable loading unit 16. The IMA is joined to a coronary artery (not shown) to form an anastomosis by applying a series of non-penetrating clips thereto. The clips which are supported on detachable loading unit 16 are deformed simultaneously by actuation of the handle assembly 12 as will be described in greater detail below. The clips secure the vascular tissue without piercing it. Detachable loading unit 16 is configured to release the IMA subsequent to the anastomosis.

Handle assembly 12 generally includes a handle housing 20 which is formed from a pair of housing halves 22a and 22b and a pair of handles 24 pivotally affixed to handle housing 20. Handle assembly 12 additionally includes a lock slider 26 which is longitudinally movable within lock slider slots 28 formed in housing halves 22a and 22b. By moving lock slider 26 distally, detachable loading unit 16 is firmly affixed to distal end 18 of body portion 14. Handle assembly 12 additionally includes a handle lockout button 30 which, when depressed inwardly with respect to handle housing halve 22a, allows handles 24 to be compressed inwardly toward handle housing 20. By compressing handles 24 inwardly toward housing 20, the surgical clips are deformed to secure the IMA to the harvested vessel in a manner described in more detail hereinbelow.

Handle assembly 12 additionally includes a collar lever 32 which projects through a collar lever slot 34 formed in housing half 22a. Collar lever slot 34 generally includes a transverse portion 36 and a longitudinally extending portion 38. When collar lever 32 resides within the transverse portion 36 of collar lever 34, the IMA is held within the detachable loading unit 16. However, after completing the anastomosis of the IMA to the left anterior descending artery (LAD), as collar lever 32 is rotated transversely through transverse portion 36 and is advanced distally through longitudinal portion 38, the IMA is released from the detachable loading unit 16 in a manner described in more detail hereinbelow.

Figure 2:
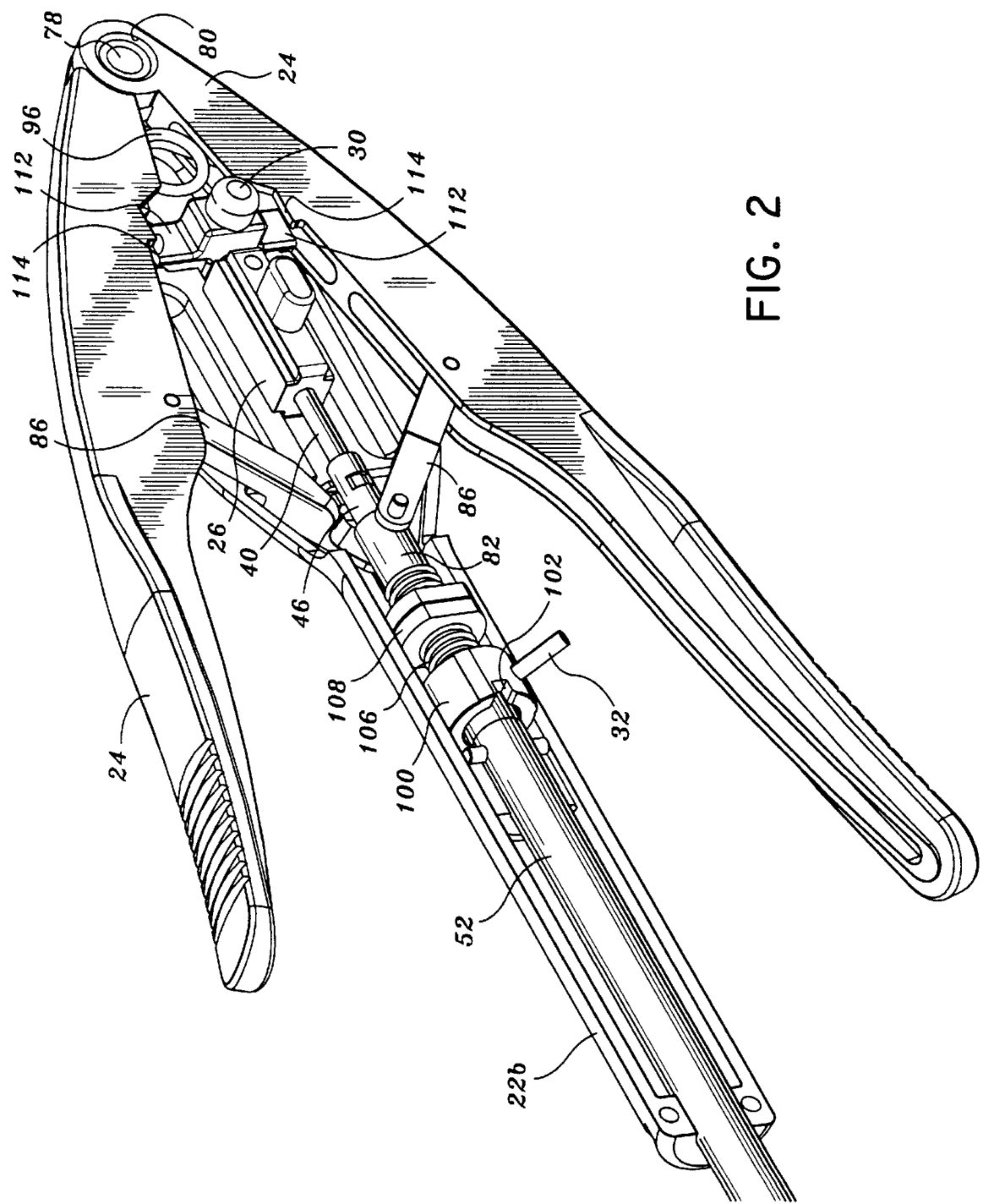
FIG. 2 is a perspective view of the handle assembly with a housing half removed.
Figure 3:
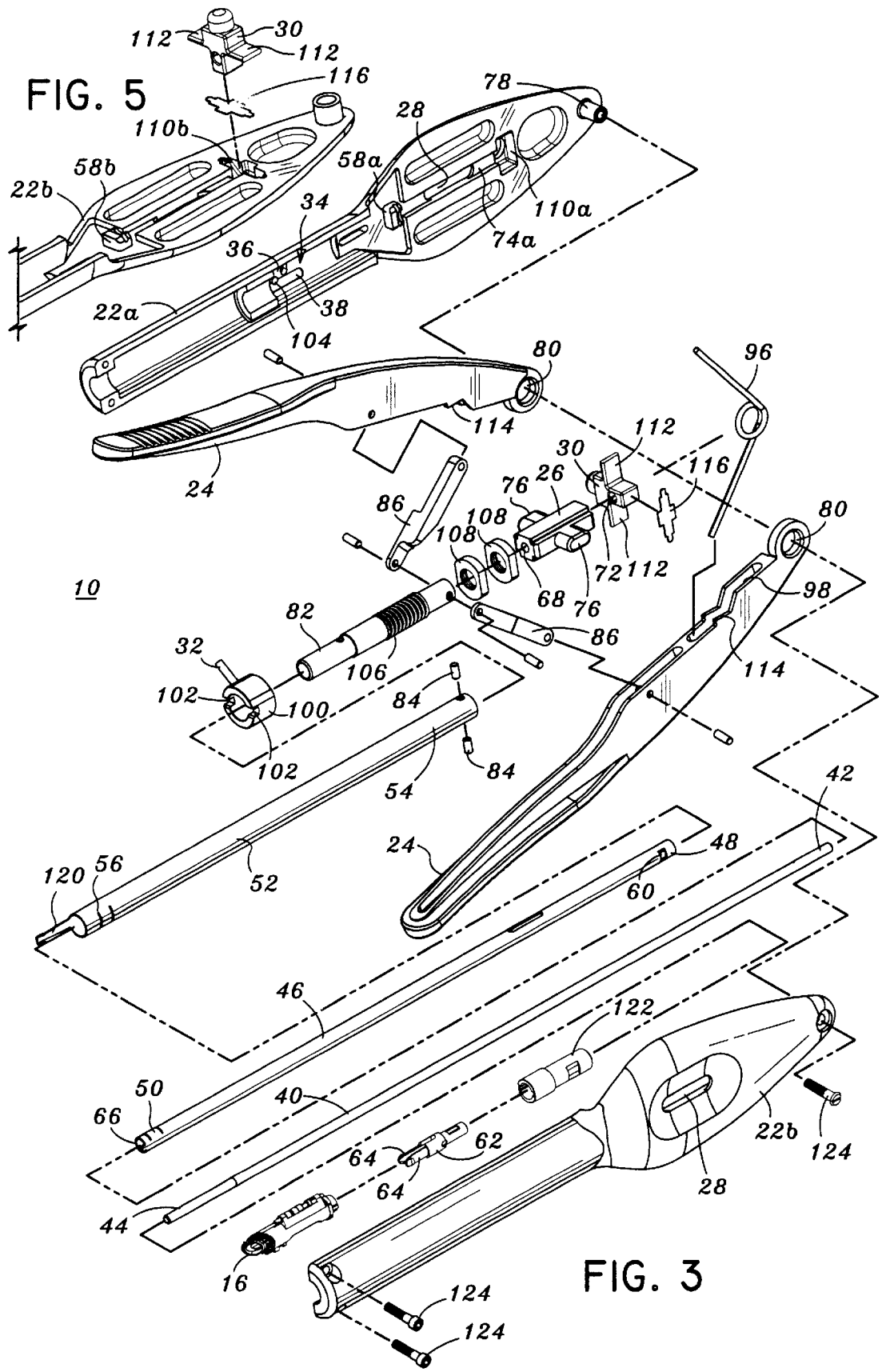
FIG. 3 is a perspective view, with parts separated, of the surgical instrument of FIG. 1.

Referring now to FIGS. 2–4, body portion 14 generally includes a center rod 40 having a proximal end 42 and a distal end 44 and an anvil support or central tube 46 having a proximal end 48 and a distal end 50. Body portion 14 additionally includes a pusher tube 52 having a proximal end 54 and a distal end 56. Projections 58a and 58b (FIG. 5) formed in housing halves 22a and 22b engage slots 60 on central tube 46 to hold the central tube 46 stationary with respect to handle housing 20. A central tube tip 62 is mounted on distal end 50 of central tube 46. Central tube tip 62 includes a pair of flexible arms 64 which are engagable with detachable loading unit 16. Center rod 40 is slidably mounted within a bore 66 of central tube 46. Proximal end 42 of center rod 40 extends through a bore 68 in lock slider 26 and is secured therein by means of a pin 70 (FIG. 4). Center rod 40 is slidable within a bore 72 of handle lockout button 30. As noted hereinabove, lock slider 26 is slidably mounted within housing halves 22a and 22b. Specifically, lock slider 26 slides within channels 74a and 74b formed in housing halves 22a and 22b. Wings 76 of lock slider 26 project through lock slider slots 28 in housing halves 22a and 22b. Thus, by moving wings 76 with respect to housing halves 22a and 22b center rod 40 is reciprocated within central tube 46.

Handles 24 are pivotally mounted to handle housing 20 by a handle pivot stud 78 formed on housing halve 22a which extends through pivot holes 80 on handles 24. Portions of handles 24 may be grooved, ridged or otherwise textured to facilitate gripping by the hand of the user.

Pusher tube 52 is movably mounted with respect to handle housing 20. Specifically, proximal end 54 of pusher tube 52 is affixed to a pusher bushing 82 by means of pins 84. Handle links 86 extend between handles 24 and pusher bushing 82. Handle links 86 are affixed at their proximal ends 88 to an intermediate portion of handles 24 by means of pins 92. Handle links 86 are affixed at their distal ends to pusher bushing 82 by means of pins 94. Handles 24 are biased away from handle housing 20 by means of a spring 96 which resides in slots 98 in each of handles 24. Compressing handles 24 inwardly toward handle housing 20 against the bias of spring 96 drives pusher bushing 82 and thus pusher tube 52 distally relative to handle housing 20 to actuate surgical instrument 10 and crimp clips about the IMA and LAD as described in detail below.

A release collar 100 is slidably mounted over pusher bushing 82. Collar lever 32 extends from release collar 100 through collar lever slot 34 formed on housing halve 22a. Release collar 100 includes release notches 102 which, when released lever 100 has been rotated, allows release notches 102 to slide over projections 104 formed on housing halves 22a and 22b. In this manner, an additional amount of distal movement of pusher tube 52 is available to release the IMA from detachable loading unit 16 in a manner discussed in more detail hereinbelow.

Pusher bushing 82 additionally includes a threaded surface 106. A pair of adjusting collars 108 are provided to be threaded onto threaded surface 106. Adjusting collars 108 are provided to engage release collar 100 and thus limit the distal advance of pusher bushing 82 and pusher tube 52. By limiting the distal advancement of pusher tube 52, the amount of crimp applied to surgical clips positioned within detachable loading unit 16 may be precisely controlled. Optionally, however, pusher bushing 82 may be formed with a projection affixed thereon or integrally formed therein to engage release collar 100 and limit the amount of travel of pusher tube 52.

As noted above, handle assembly 12 additionally includes a handle lockout button 30 which prevents movement of handles 24 until handle lockout button has been depressed inwardly with respect to handle housing 20. Specifically, handle lockout button 30 is slidably mounted within slots 110a and 110b (FIG. 5) formed in housing halves 22a and 22b respectively. Handle lockout button 30 includes projections or wings 112 which engage surfaces 114 formed on handles 24 and prevent handles 24 from being closed toward handle housing 20. A leaf spring 116 is affixed between handle housing 22b and handle lockout button 30 (FIG. 5) and biases handle lockout button 30 into the blocking position engaging wings 112 with handle locking surfaces 114 as shown in FIG. 6. Depressing handle lockout button 30 against the bias of spring 116 allows wings 112 to clear handle locking surfaces 114 and thereby allow wings 112 to move into slots 98 in handles 24 and allow handles 24 to close against handle housing 20.

Referring again to FIG. 3, a camming arm 120 extends from distal end 56 of pusher tube 52. Camming arm 120 is configured to engage corresponding structure on detachable loading unit 16 in order to crimp clips about tissue and assist in a return stroke of a pusher in a manner described hereinbelow. Additionally, a distal pusher sleeve 122 is affixed to distal end 56 of pusher tube 52. Pusher tube 52 including pusher sleeve 122 are slidable over central tube 46 and central tube tip 62. Housing halves 22a and 22b are preferably secured together by any suitable means and preferably by means of screws 124 (FIG. 4).

Figure 7:
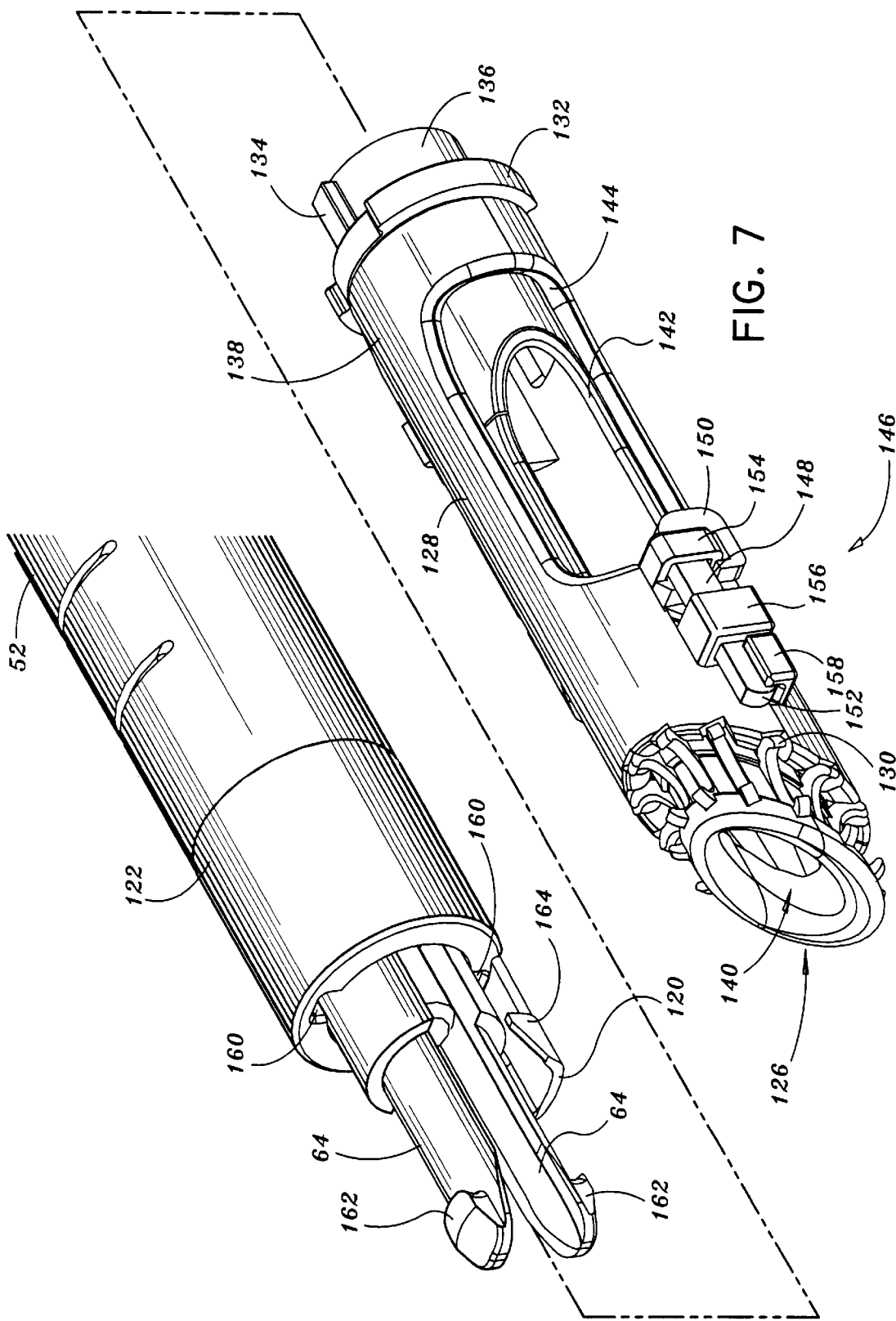
FIG. 7 is a perspective view of the distal end of a body portion of the apparatus of FIG. 1 and a detachable loading unit containing a plurality of surgical clips.

Referring now to FIG. 7, the novel detachable loading unit suitable for use with the surgical instrument 10 will now be described. Detachable loading unit 16 is particularly useful in installing the IMA into a coronary artery such as the LAD. Detachable loading unit 16 generally includes a fastener support or anvil 126 and a fastener camming member or pusher 128 slidably and concentrically mounted about anvil 126. A plurality of surgical clips 130 are held between anvil 126 and pusher 128. An example of the clips which can be used are disclosed in U.S. patent application Ser. No. 08/311,049, filed Sep. 23, 1994, the contents of which are incorporated herein by reference. Movement of pusher 128 distally with respect to anvil 126 crimps surgical clips 130 about tissue. Surgical clips 130 are secured between pusher 128 and anvil 126 by a locking disk 132 which slides over and engages an abutment 134 provided at a proximal end 136 of anvil 126. Locking disk 132 presses against a proximal end 138 of pusher 128 to secure the clips on DLU 16. Together anvil 126 and pusher 128 define a bore 140 for receipt of a length of IMA therein. Additionally, exits 142 and 144 formed in anvils 126 and pusher 128, respectively, provide openings through which the length of the IMA may extend.

By positioning surgical clips 130 and the length of IMA within detachable loading unit 16, detachable loading unit 16 can be easily manipulated within an operative area to initially position the surgical clips and the IMA in a position to form an anastomosis between the IMA and an LAD. It should be noted that multiple detachable loading units 16 may be provided for use with surgical instrument 10 to allow multiple anastomosis to be made with a single instrument. Additionally, detachable loading unit 16 can be configured to be reloadable, that is, after firing detachable loading unit 16, it may be disassembled and another plurality of surgical clips positioned thereon.

In order to facilitate removal of the IMA from detachable loading unit 16 after forming an anastomosis, detachable loading unit 16 is provided with a latch mechanism 146 which generally includes a latch 148 having a clip portion 150 and a leg portion 152 extending distally from clip portion 150. Latch 148 extends through a first mount 154 formed on anvil 126 such that clip portion 150 secures latch 148 to first mount 154. Leg portion 152 of latch 148 extends distally through a second mount 156 formed on pusher 128 and rests against a catch 158 formed on pusher 128. Movement of pusher 128 such that catch 158 no longer engages leg portion 152 facilitates partial disassembly of detachable loading unit 16 to release the IMA after anastomosis.

In addition to securing locking disk 132 against proximal end 138 of pusher 128, abutments 134 additionally function as an alignment device and are configured to fit within notches 160 formed in pusher sleeve 122.

Flanges 162 formed on arms 64 facilitate securing surgical instrument 10, and in particular, central tube 46 to anvil 126. Additionally, projections 164 on camming arm 120 facilitate securing pusher tube 52 to pusher 128.

Figure 8:
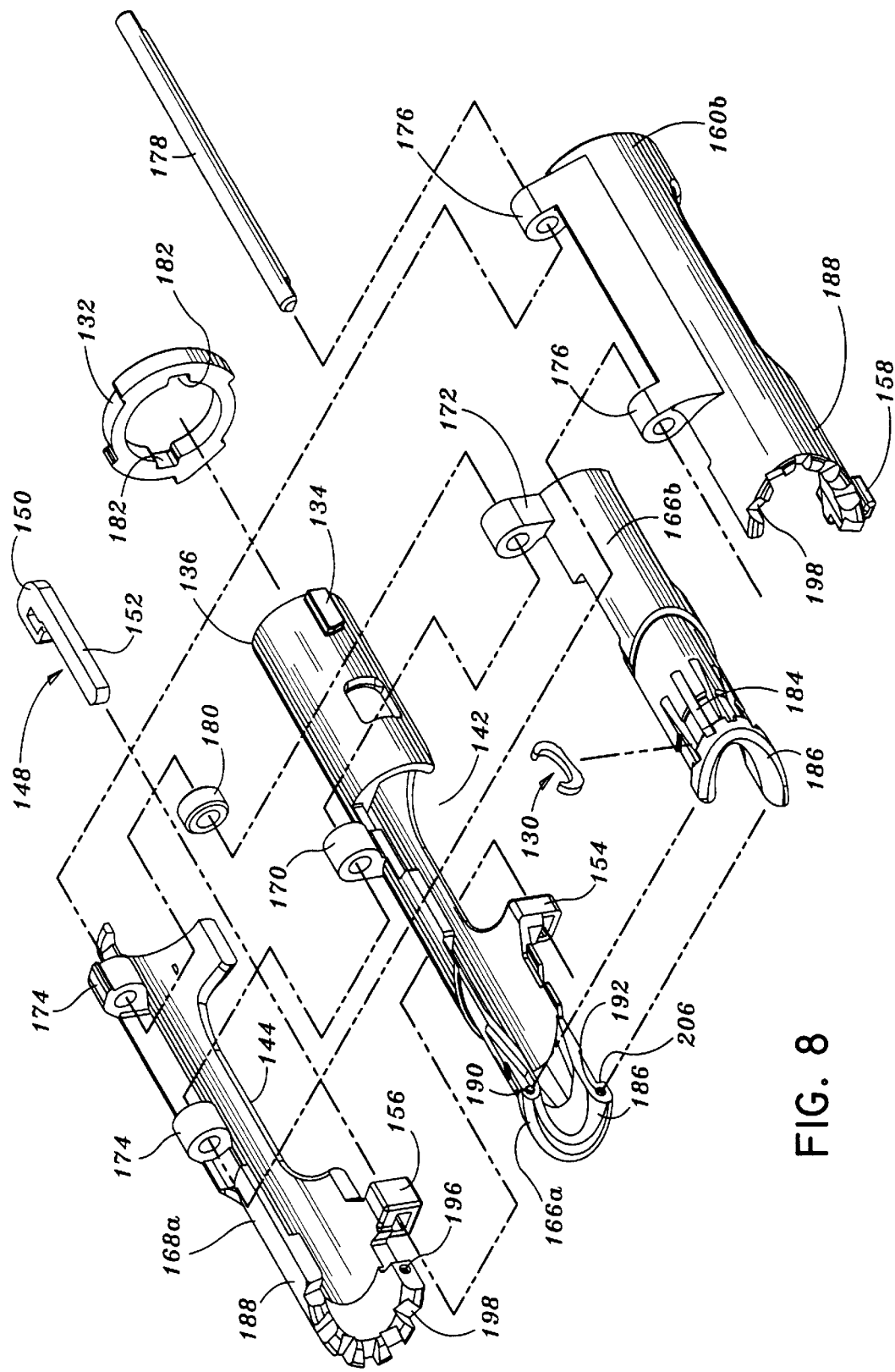
FIG. 8 is a perspective view of the detachable loading unit, with parts separated.

Referring now to FIG. 8, anvil 126 is preferably formed as a pair of anvil halves 166a and 166b. Similarly, pusher 128 is preferably formed of pusher halves 168a and 168b. Anvil half 166a preferably includes a mount 170 while anvil half 166b includes a mount 172. Similarly, pusher half 168a includes a pair of pusher mounts 174 while pusher half 168b includes a pair of pusher mounts 176. Anvil halves 166a and 166b and pusher halves 168a and 168b are pivotally connected together by means of a pivot pin 178 which extends through anvil mounts 170, 172 and pusher mounts 174, 176 and defines a common pivot point.

Figure 9:
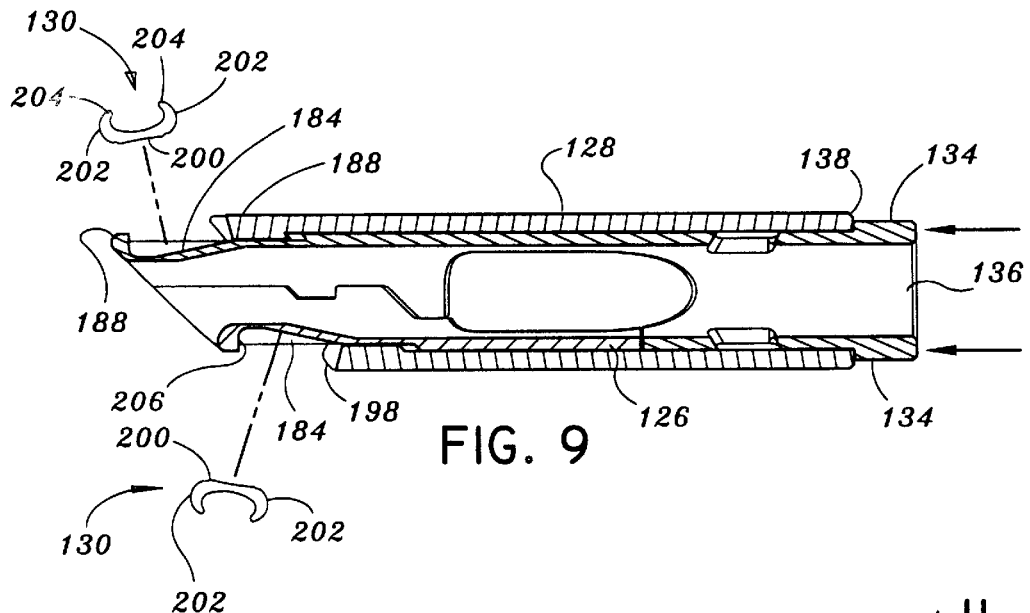
FIG. 9 is a sectional view of the detachable loading unit prior to installation of surgical clips therein.

As noted above, latch mechanism 146 is provided to release the IMA after anastomosis. Specifically, when latch 146 engages catch 158 anvil halves 166a and 166b and pusher halves 168a and 168b are secured together to form a unitary structure. When leg portion 152 is disengaged from catch 158, anvil half 166b and pusher half 168b may be pivoted away from anvil half 166a and pusher half 168a to facilitate removal of the IMA after anastomosis. A bushing 180 is provided on pivot pin 178 and aids in limiting the stroke of pusher 128 so that it does not contact camming edges 206 on anvil 126 (FIG. 9). Locking disk 132 includes a pair of notches 182 which are provided to slide over abutments 134. After sliding locking disk 132 over abutments 134, the locking disk may be rotated to move notches 182 out of alignment with abutment 134 (FIG. 11) and secure clips 130 on anvil 126.

Clips 130 are frictionally or compressionally secured between pusher 128 and anvil 126. Clips 130 reside within a plurality of circumferentially spaced, longitudinal channels 184 formed in a distal end 186 of anvil halves 166a and 166b. A distal end 188 of pusher 128 engages clips 130 to retain them within channels 184. A pair of opposed pins 190 and detents 192 formed in anvil halves 166a and 166b ensure appropriate alignment of the distal end 186 of anvil 126. Similarly, a pin 184 engages a detent 196 formed on pusher halves 168a and 168b to appropriately align pusher halves 168a and 168b in the closed configuration. Distal end 188 of pusher 128 includes a plurality of camming edges 198.

Referring now to FIG. 9, clips 130 generally include a crown portion 200 having a pair of legs 202a and 202b extending distally therefrom. Each leg 202a and 202b terminates in a rounded atraumatic tip 204a and 204b. In order to install clips 130 on detachable loading unit 16, pusher 128 is initially positioned in a generally proximal orientation relative to anvil 126 to allow surgical clips 130 to be individually inserted into longitudinal channels 184 formed in anvil 126. Camming edges 206 are formed on anvil 126 to engage clips 130.

Figure 10:
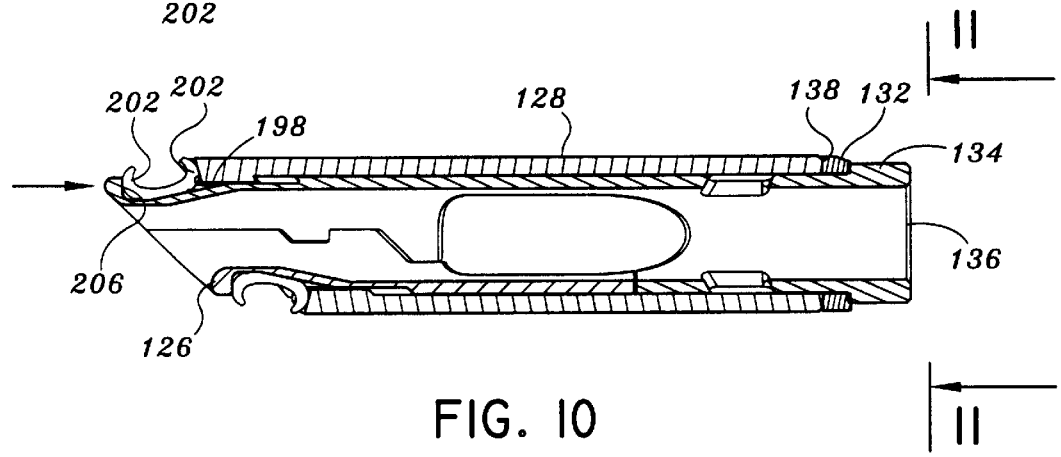
FIG. 10 is a view similar to FIG. 9 with the surgical clips loaded onto the detachable loading unit.

Referring to FIG. 10, once clips 130 have been positioned within channels 184, pusher 128 is advanced distally until camming edges 198 secures surgical clips 130 between camming edges 198 of pusher 128 and camming edges 206 of anvil 126.

Figure 11:
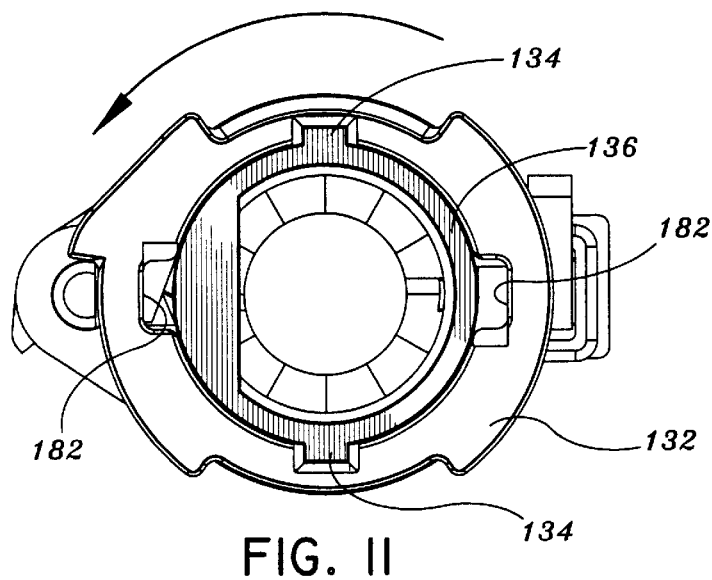
FIG. 11 is a view taken along line 11—11 of FIG. 10 and illustrating a locking disk to secure the surgical clips within the detachable loading unit.

Referring now to FIGS. 10 and 11, once clips 130 have been secured within channels 184, locking disk 132 may be positioned on the proximal end 136 of anvil 126 and slid over abutments 134. Locking disk 132 engages proximal end 138 of pusher 128 and, upon rotation of locking disk 132 to bring notches out of alignment with abutments 134, and firmly cams pusher 128 distally to secure clips 130 within channels 184.

Figure 12:
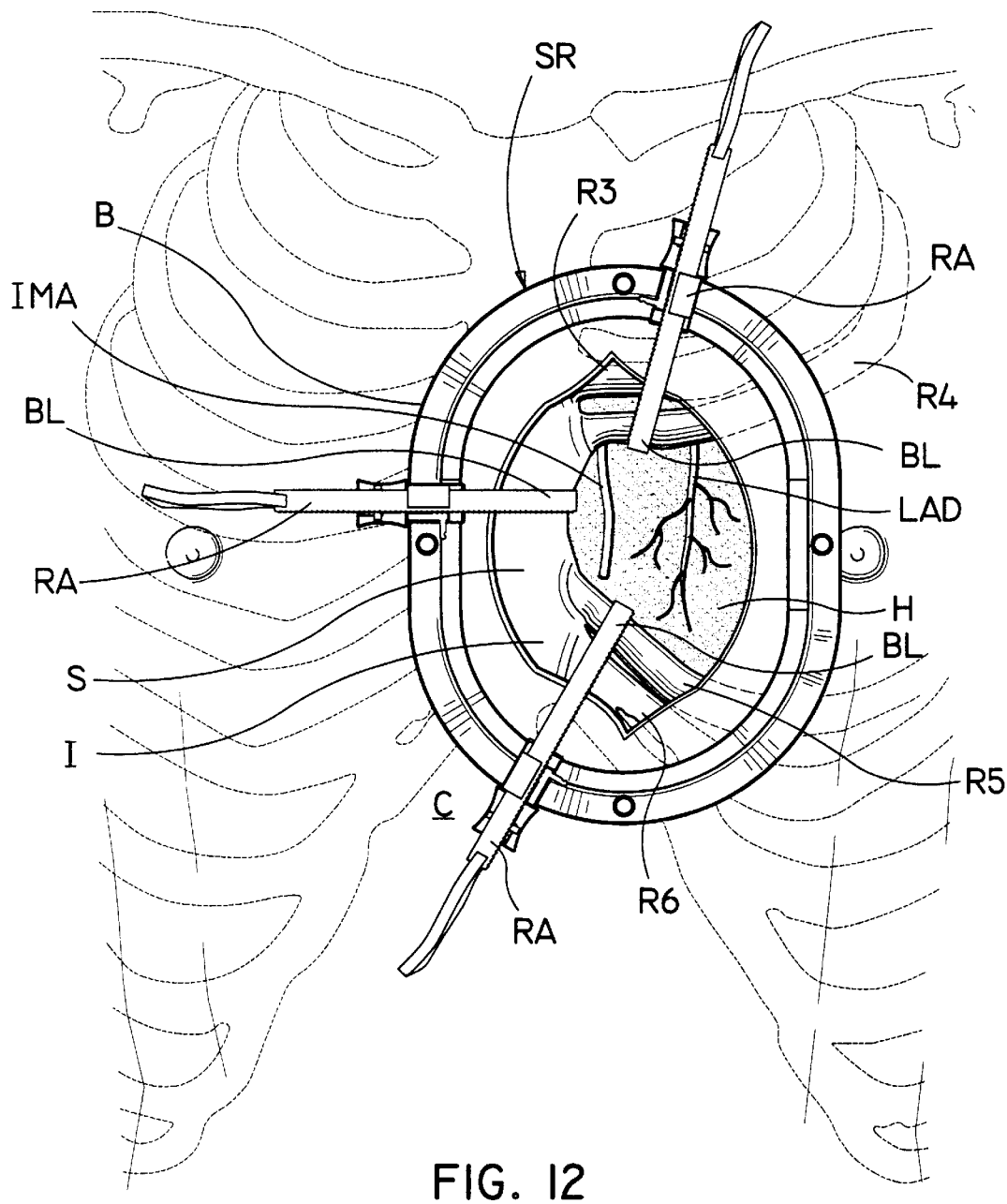
FIG. 12 is a top view in reduced scale of a surgical retractor placed on a patient's chest to provide access to the heart.

Turning now to FIGS. 12–39, the operation of surgical instrument 10 and DLU 16 will now be described. Surgical instrument 10 and DLU 16 may be used in conventional open CABG procedures using a median sternotomy or other large incision without stopping the heart. Alternatively, the thoracic "window" procedure may be used to achieve access. The "window" approach involves a smaller incision and less displacement of the ribs, and therefore is less traumatic to the patient. Referring initially to FIG. 12, for this approach, conventional surgical techniques are used to determine the location of the incision I accessing chest cavity C. A surgical retractor, such as surgical retractor SR is used to access the heart and coronary arteries by creating the "window". Base B is placed on the chest of the patient with the opening of base B overlying the operative site. Incision I is made, exposing several ribs $R_3$, $R_4$, $R_5$, $R_6$.

Retractor assemblies RA are mounted to base B at various locations. Each of retractor assemblies RA includes blade BL having a hook to engage a rib therewith. Blade BL is positioned around a rib, which is deflected and retracted by moving blade BL radially outward. Additional retractor assemblies RA are mounted and used to retract ribs until a sufficiently large opening O in chest cavity C is defined to provide access to the heart. For example, sternum S and fourth rib $R_4$ and fifth rib $R_5$ can be spread apart to create a window. Alternatively, fourth rib $R_4$ and fifth rib $R_5$ are cut from sternum S and spaced to create a larger window. Alternatively, a fifth rib $R_5$ can be cut, and sternum S and fourth rib $R_4$ and sixth rib $R_6$ are spread. Base B is at least partially held in position over the operative site by tension created in retracting the ribs by retractor blades BL.

The internal mammary artery (IMA) is dissected from surrounding cartilage and muscle, and a free end is exposed. The coronary artery, e.g. the left anterior descending artery (LAD), is then prepared for receiving IMA graft. The heart H is positioned either by traction sutures passing through the pericardium or by manipulation instruments which are held by surgical personnel or clamped to the operating table or to base B. Blood flow through the LAD can be restricted by cardiopulmonary bypass and pericardial cooling. Alternatively, a clamping instrument may be applied directly on the LAD to restrict blood flow and reduce movement of the heart near the LAD.

Figure 13:
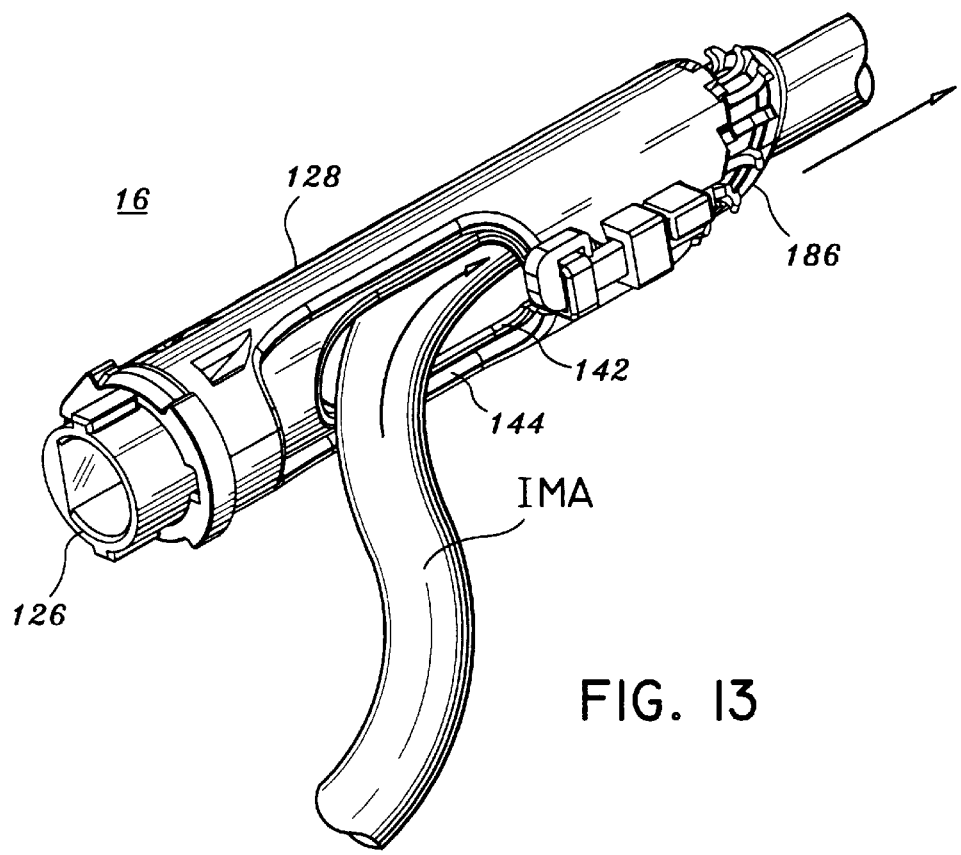
FIG. 13 is a perspective view of a section of a harvested vessel being positioned within the detachable loading unit.
Figure 14:
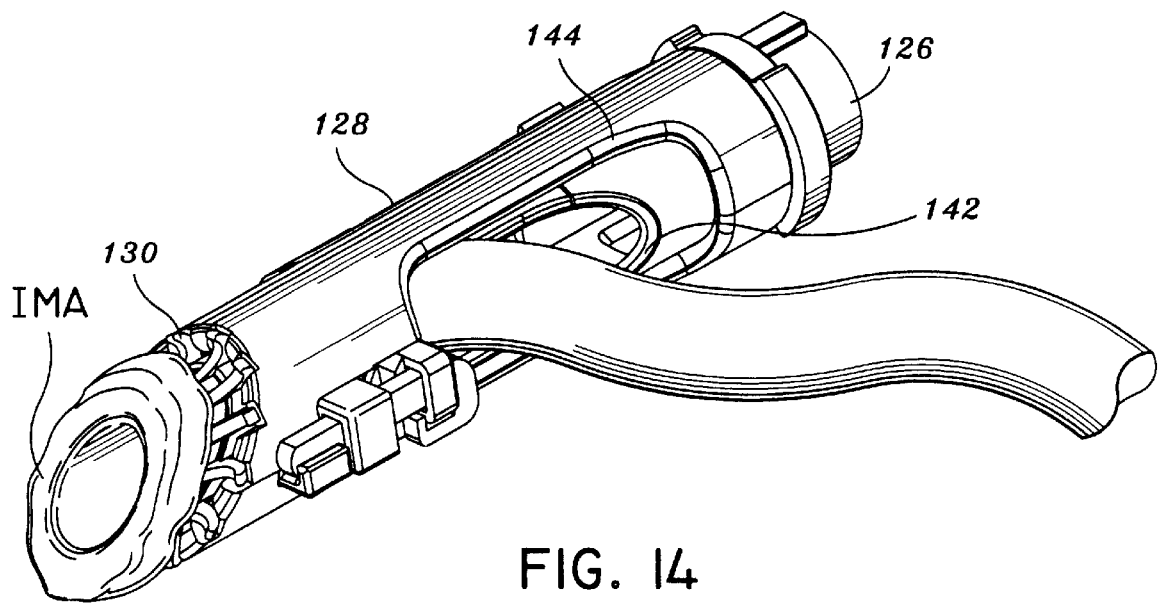
FIG. 14 is a view of the harvested vessel with one end everted about the distal end of the detachable loading unit.
Figure 15:
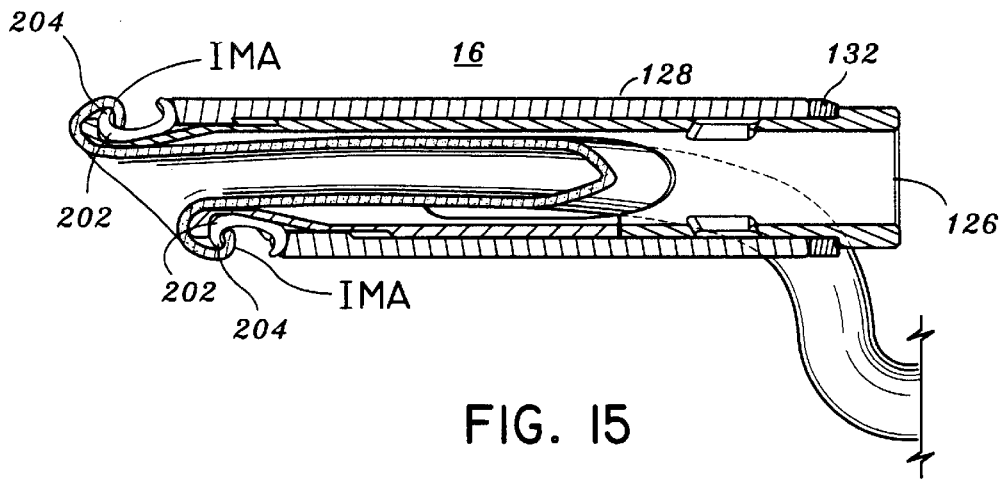
FIG. 15 is a sectional view illustrating the harvested vessel installed within the detachable loading unit.

Referring now to FIG. 13, the IMA is prepared for grafting to the LAD. A free end of the IMA is inserted through exit 144 in pusher 128 and exit 142 in anvil 126 such that the free end of the IMA protrudes beyond distal end 186 of anvil 126. Next, as shown in FIG. 14, the free end of the IMA is everted around the distal end 186 of anvil 126. In particular, tweezers (not shown) may be used to manually invert the IMA. Alternatively, the actuated grasping instrument such as ENDO-GRASP instrument (not shown) manufactured by U.S. Surgical Corporation of Norwalk, Conn. may be used. The IMA is grasped and stretched over a distal end 186 of anvil 126. As shown in FIG. 15, the IMA is engaged by a leg 202 of clips 130 to hold the vessel in place. Care should be exercised to insure that the IMA has been engaged by a leg 202. Elasticity of the IMA provides a compression about anvil 126 in the everted configuration.

Figure 16:
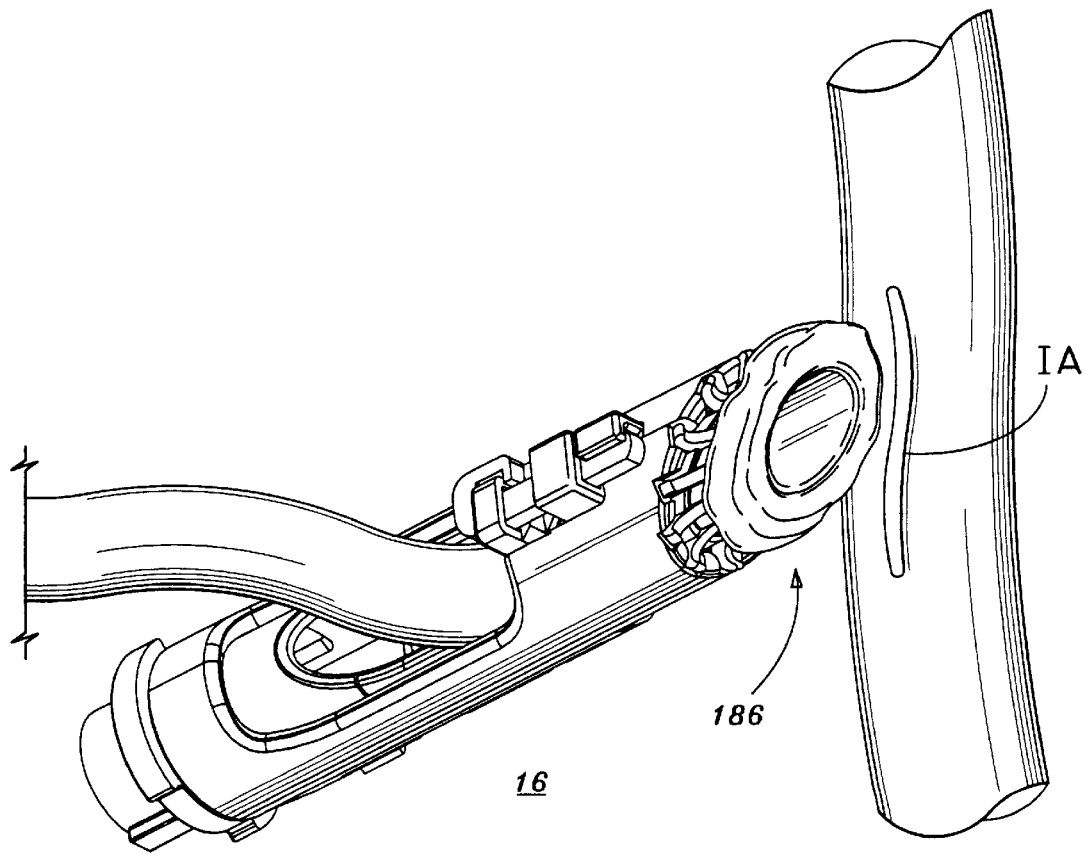
FIG. 16 is a perspective view of the detachable loading unit with the harvested vessel installed thereon and in a position to be inserted within an incision in the coronary artery.

Referring now to FIG. 16, FIG. 16 illustrates the LAD prepared to receive the IMA. An incision IA is made in the LAD downstream from the occlusion. DLU 16 is manipulated such that distal end 186 of anvil 126, carrying everted IMA, is approximated with incision IA in the LAD.

Figure 17:
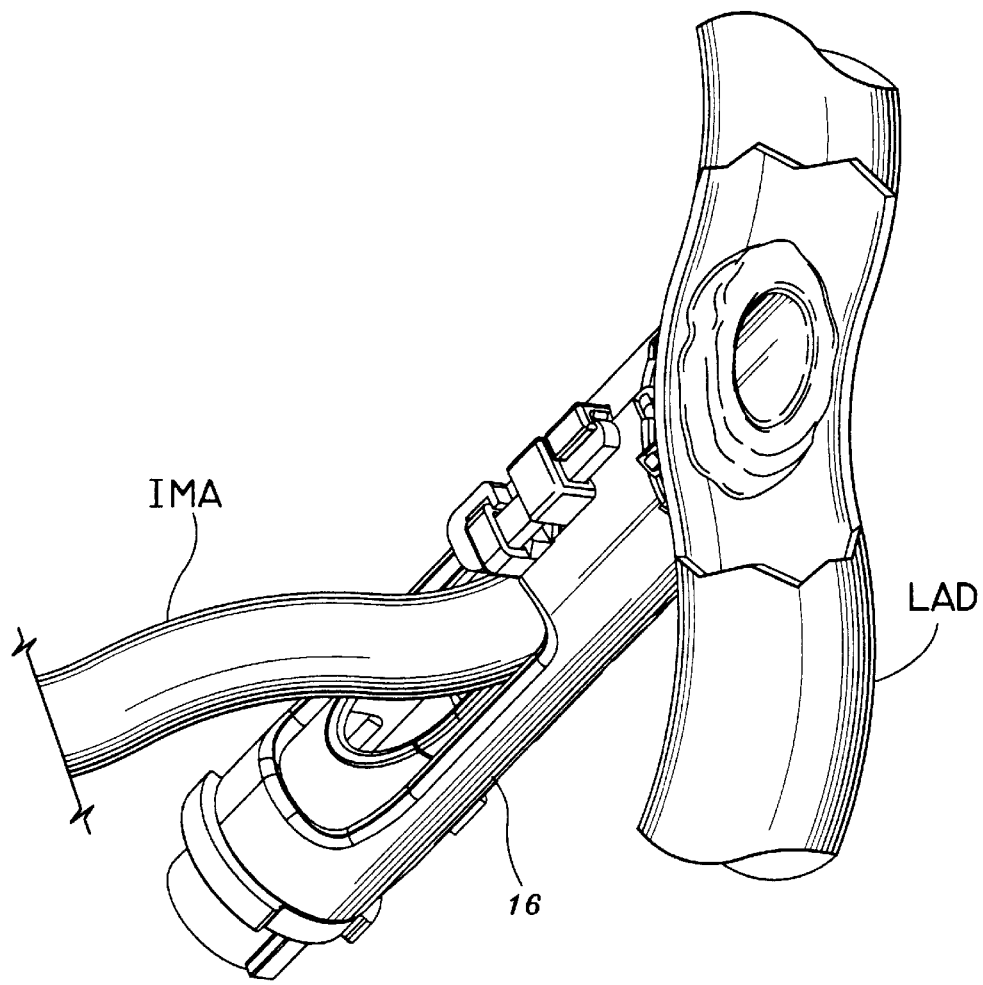
FIG. 17 is a view of the detachable loading unit with everted harvested vessel thereon positioned within the coronary artery.
Figure 18:
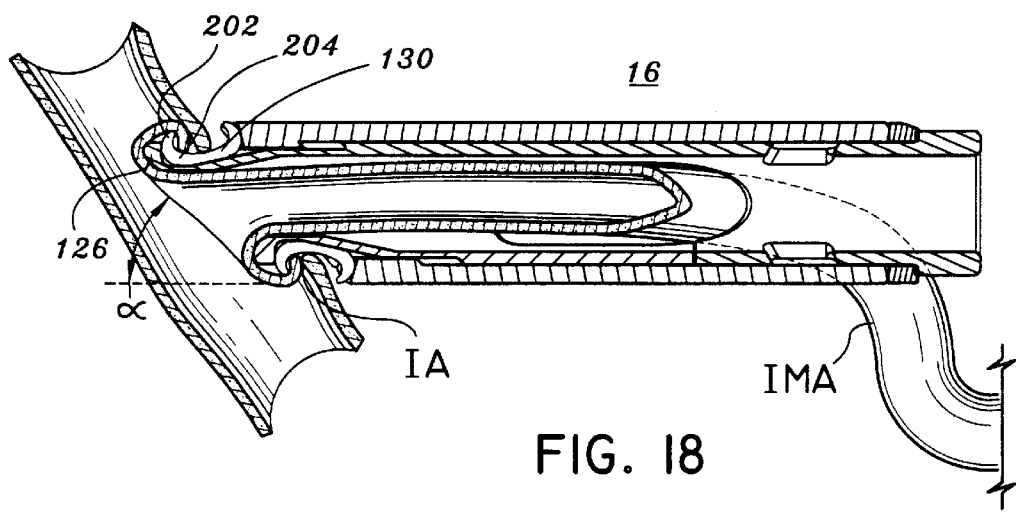
FIG. 18 is a sectional view of the detachable loading unit with harvested vessel installed thereon and positioned within the coronary artery.

The everted IMA is inserted into incision IA of the LAD (FIG. 17). As shown in FIG. 18, the distal end 186 of anvil 126 is oriented at an angle α in order to optimize the end-to-side anastomosis and to facilitate blood flow across the graft from the IMA to the LAD. This junction creates an acute or obtuse angle between the vessels. The distal end portion of anvil 126 including everted IMA and clips 130 are inserted into incision IA in the LAD. The radial orientation of legs 202 and atraumatic tips 204 permit clips 130 to be inserted atraumatically into the LAD. Elasticity of the LAD closes incision IA about anvil 28.

Upon insertion, the surgeon retracts DLU 16 to apply proximal force to DLU 16. Such force permits the side wall of the LAD surrounding incision IA to be positioned between leg portions 152 of clips 130. By retracting 16, incision IA is forced to assume a circular shape corresponding to the circular cross-section of anvil 126 and makes uniform contact with the everted section of the IMA. The symmetrical nature of the circular junction of IMA and LAD permits the consistent joining of the vessels about anvil 126.

Figure 19:
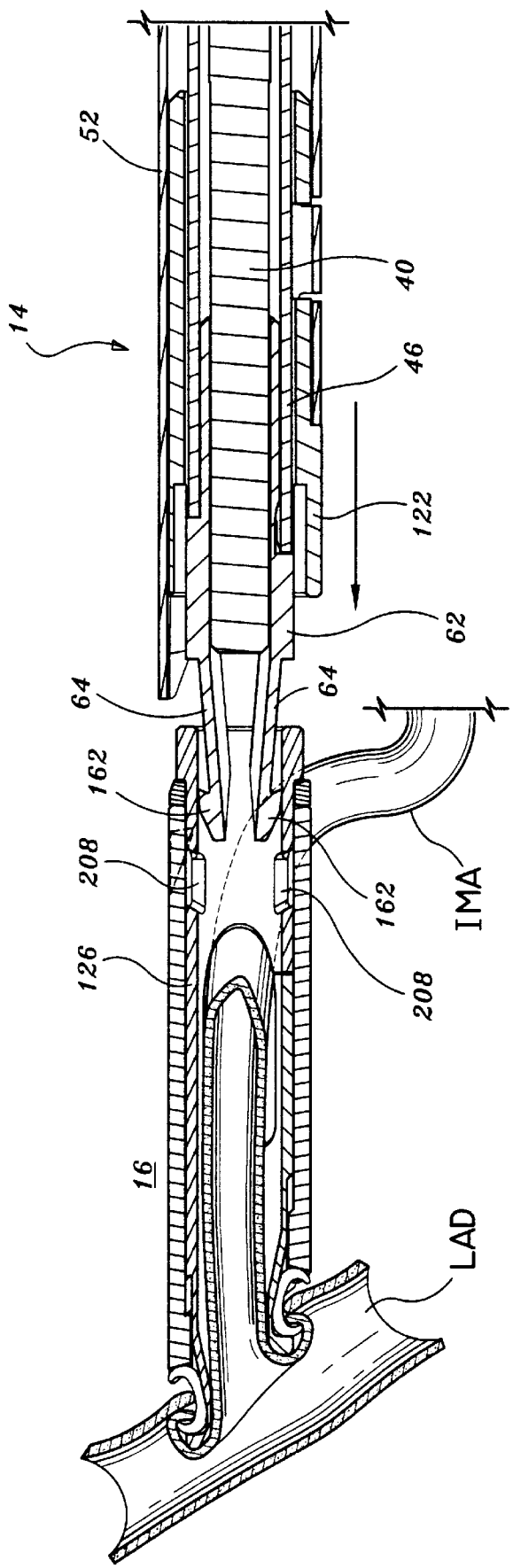
FIG. 19 is a sectional view of the distal end of the surgical instrument being inserted into the proximal end of the detachable loading unit.

Referring now to FIG. 19, surgical instrument 10 may now be connected to DLU 16 in order to close the clips about the IMA and the LAD to form the anastomosis. Specifically, surgical instrument 10 is advanced toward the DLU 16 such that central tube tip 62 and, in particular, arms 64 enter the proximal end 136 of anvil 126. Flanges 162 are advanced towards engagement notches 208 formed in proximal end 136 of anvil 126. As shown in FIG. 20, upon advancement of surgical instrument 10 toward DLU 16, flanges 162 formed on flexible arms 64, flex outwardly so as to engage engagement notches 208. In this manner, surgical instrument 10 is releasably secured to DLU 16. However, arms 64 being flexible, it is preferable to block arms 64 from flexing out of engagement notches 208 during actuation of surgical instrument 10.

Turning now to FIG. 21, lock slider 26 is advanced distally to move center rod 40 in a distal direction. It should be noted that upon distal movement of lock slider 26 and center rod 40, proximal end 42 of center rod 40 is withdrawn from bore 72 in handle lockout button 30. As shown in FIG. 22, distal advancement of center rod 40 moves the distal end 44 of center rod 40 into a position between arm 64 to fixedly secure flanges 162 within engagement notches 208. Thus, in this position, surgical instrument 10 is securely locked to DLU 16.

Referring now to FIGS. 23–33, the closure of clips 130 about IMA and LAD will now be described. Referring initially to FIG. 23, it can be seen that pusher 126 is provided with engagement notches 210 for receipt of projections 164 on carrying arm 120.

Figure 24:
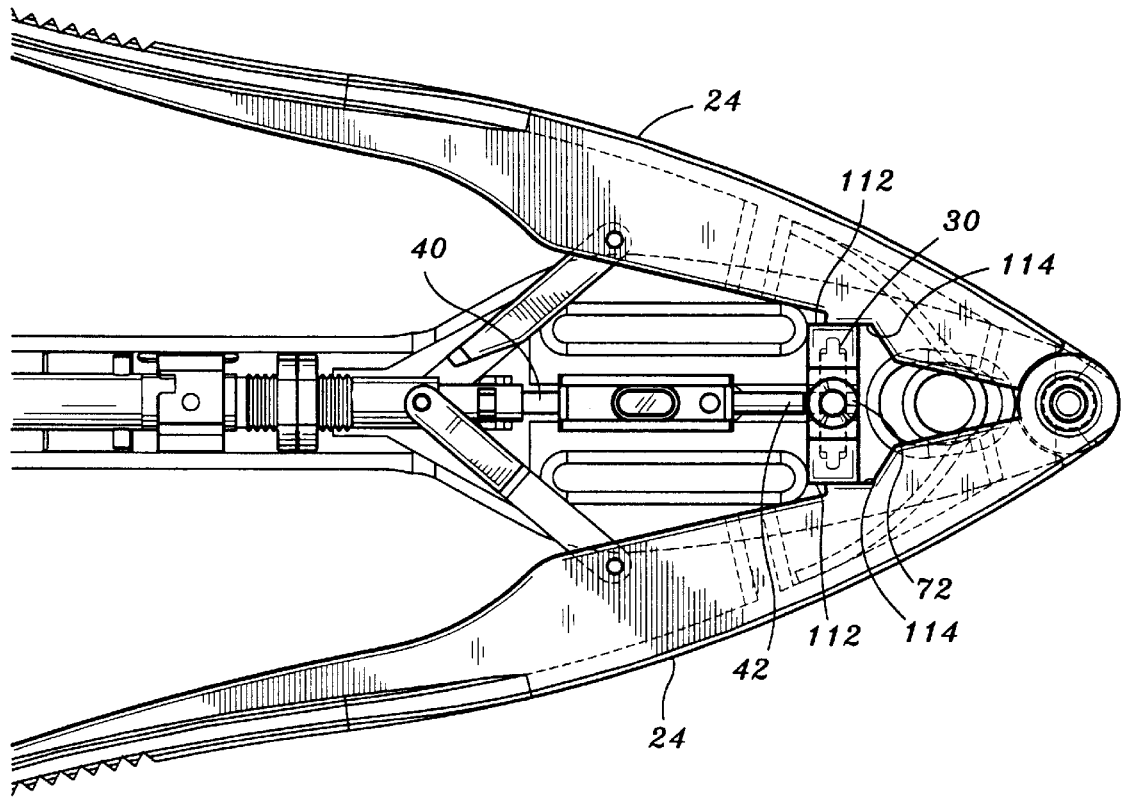
FIG. 24 is a side view, with the housing half removed, of the handle assembly and handle lockout button.
Figure 25:
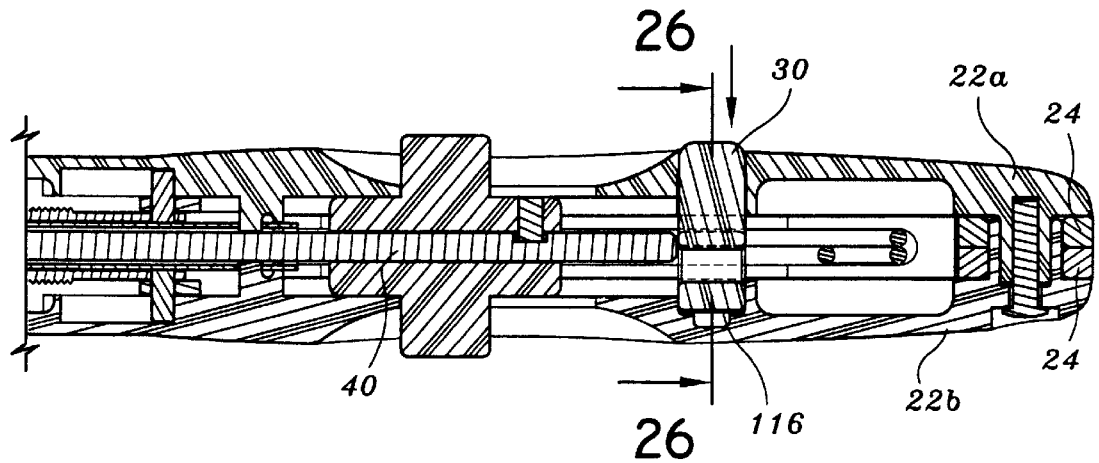
FIG. 25 is a sectional view of the handle assembly illustrating the handle lockout button being depressed and blocking the center rod.
Figure 26:
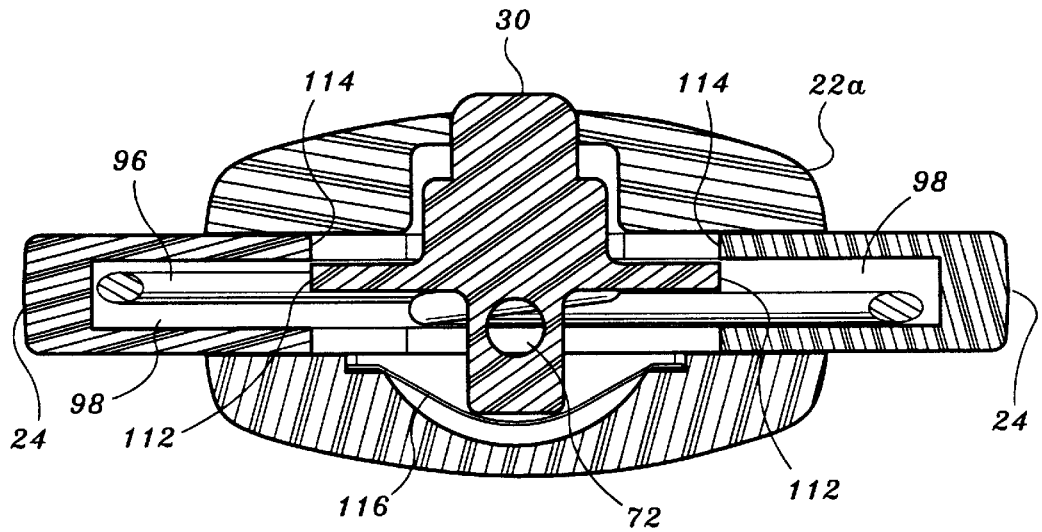
FIG. 26 is a sectional view taken along line 26—26 of FIG. 25 and illustrating the handle lockout button disengaged from the handles.

Referring to FIG. 24, as noted above, the distal advancement of center rod 40 withdraws the proximal end 42 of center rod 40 from within the bore 72 of handle lockout button 30. However, locking wings 112 on handle lockout button 30 still engage handle lock surfaces 114 on handles 24. Referring to FIGS. 25–26, in order to close handles 24, handle lockout button 30 is depressed inwardly with respect to handle housing 20. Notably, this causes handle lockout button 30 to block center rod 40 against proximal movement and inadvertent release of DLU 16. As specifically shown in FIG. 26, the depression of handle lockout button 30 against the bias of spring 116 moves locking wings 112 of handle lockout button 30 out of engagement with handle lock surfaces 114 on handles 24 thereby freeing handles 24 for movement.

Figure 27:
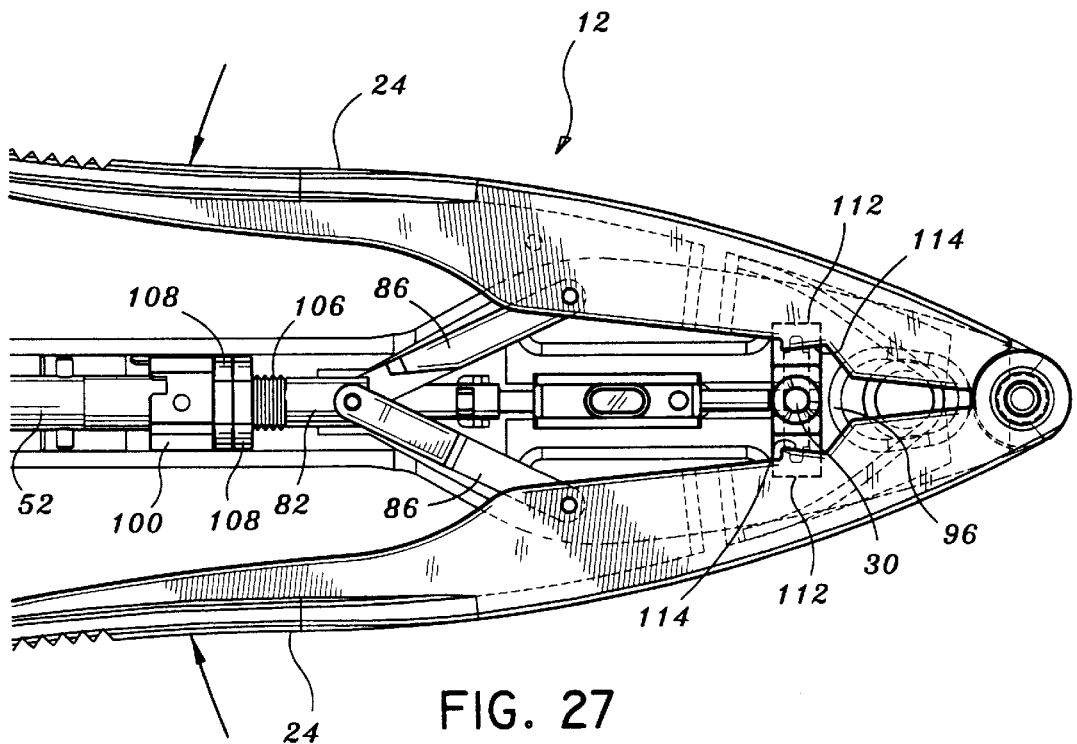
FIG. 27 is a view of the handle assembly with a housing half removed illustrating the closing of the handles to drive the pusher tube distally.

Referring to FIGS. 27 and 28, closure of handles 24 against the bias of spring 96 and towards handle housing 20 advances pusher tube 52 distally until adjusting collars 108 engage release collar 100. At this point, release collar 100 is engaged against release projections 104 formed in handle housing 20 and cannot be advanced further distally. Specifically, as shown in FIG. 29, release notches 102 on release collar 100 are out of alignment with release projections 104.

Figure 30:
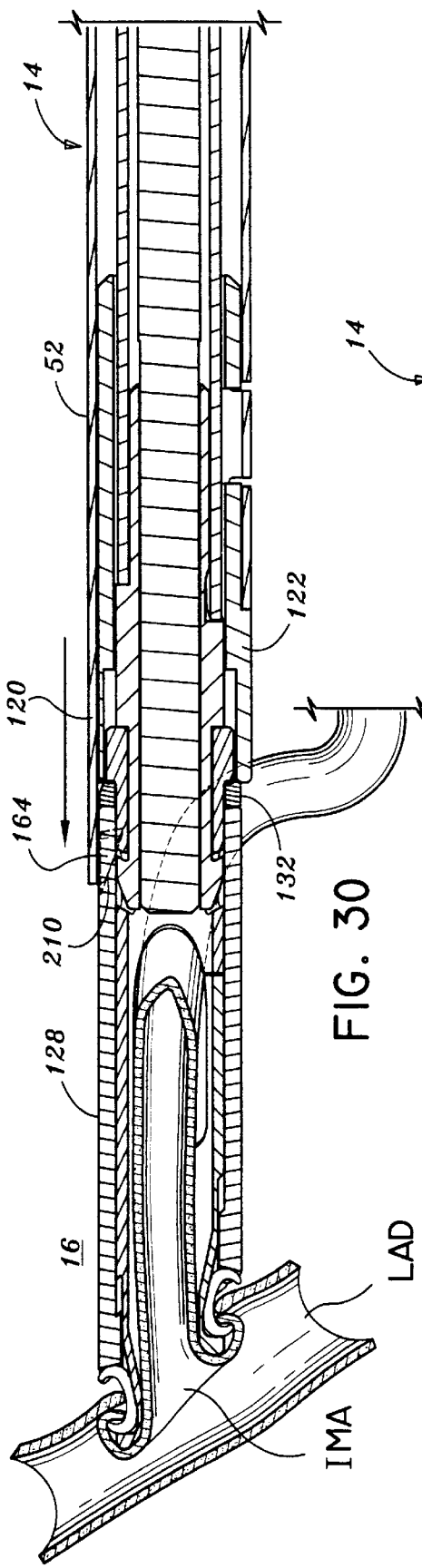
FIG. 30 is a sectional view of the distal end of the surgical instrument illustrating initial advancement of the pusher tube into engagement with the pusher of the detachable loading unit.
Figure 31:
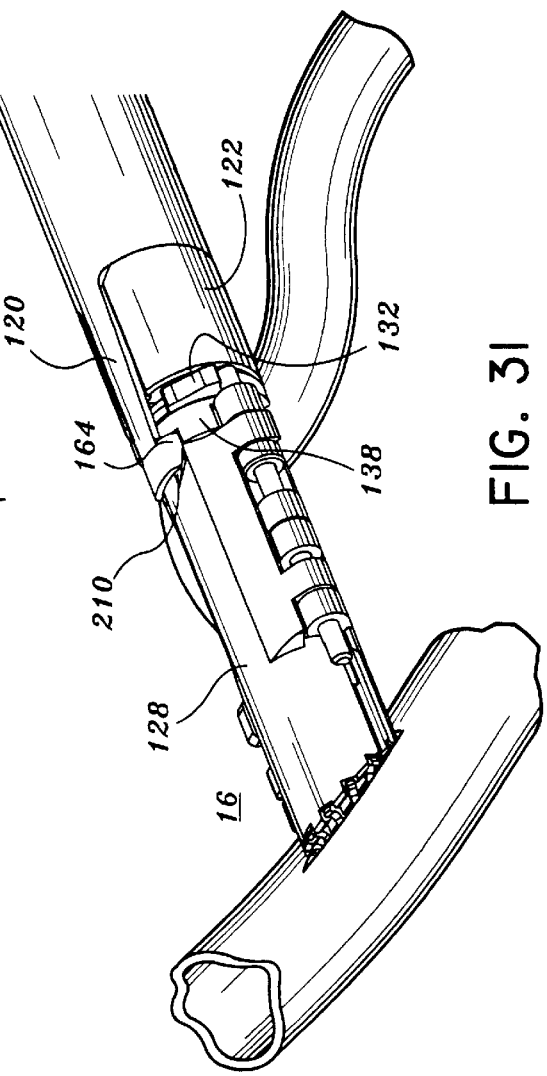
FIG. 31 is a perspective view of the distal end of the surgical instrument with the pusher tube engaged with the pusher of the detachable loading unit.

As shown in FIGS. 30 and 31, the distal advancement of pusher tube 52 moves projections 164 on camming arm 120 into engagement with engagement notches 210 formed in pusher 128. Once pusher tube 52 has been fully engaged with pusher 126, surgical instrument 10 may be further actuated by compression of handles 24 inwardly relative to handle housing 20 in order to crimp clips 130 about the IMA and LAD as shown in FIG. 33. Distal movement of pusher tube 52 forces pusher sleeve 122 against locking disk 132 thereby driving pusher 128 distally.

Referring for the moment to FIG. 32, prior to crimping clips 130, it can be seen that leg portion 152 of latch 148 is engaged with catch 158 and pusher 128. Referring now to FIG. 34, after clips 130 have been crimped, it can be seen that leg portion 152 is almost, but not entirely, disengaged from catch 158. At this point, the anastomosis has been completed. Surgical instrument 10 is moved proximally to draw DLU 16 away from the anastomosis. Specifically, anvil 126 is drawn proximally out of the LAD past the anastomosis.

Figure 35:
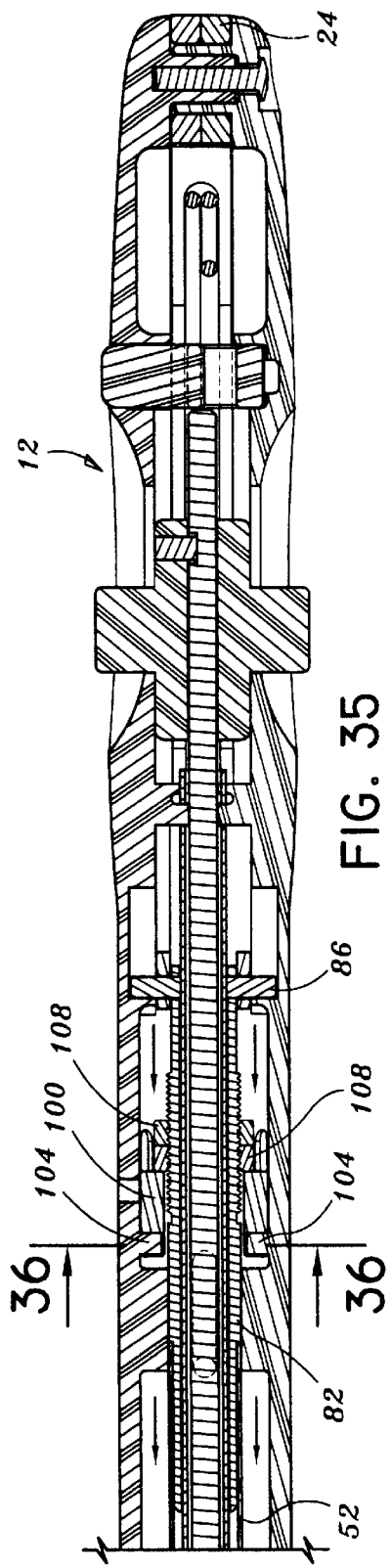
FIG. 35 is a sectional view of the handle assembly after rotation of the collar lever approximately one quarter of a turn allowing the pusher tube to move a final distance.
Figure 36:
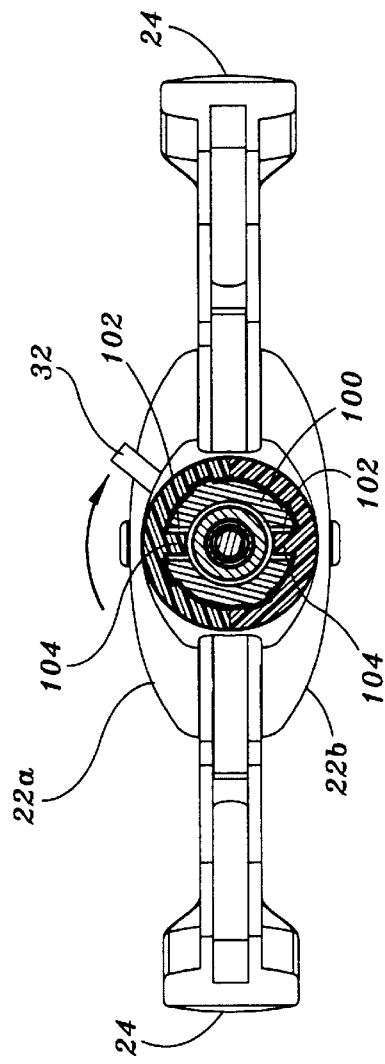
FIG. 36 is a sectional view taken along line 36—36 of FIG. 35 illustrating the rotation of the collar lever to bring the collar release notches into alignment with the projections on the housing.
Figure 37:
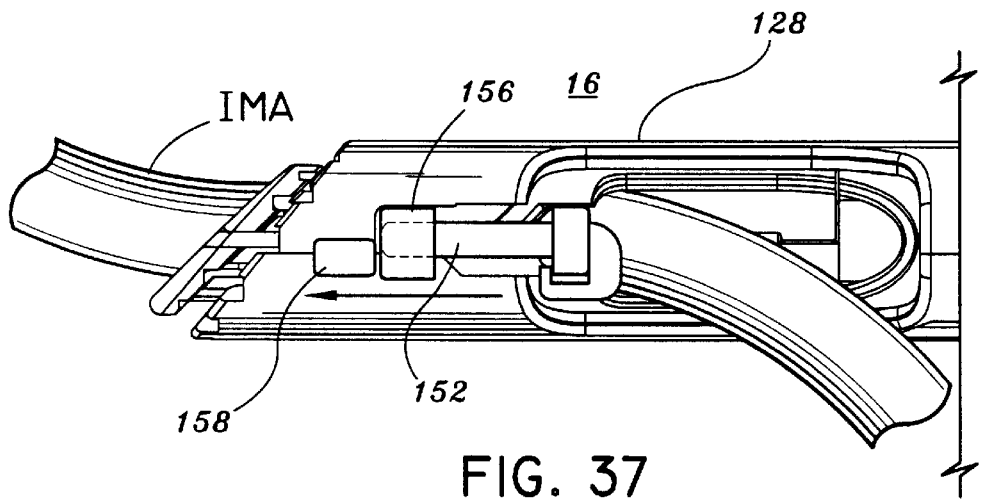
FIG. 37 is a perspective view of the detachable loading unit with the latch mechanism completely disengaged.

In order to release the IMA from DLU 16, it is necessary to unlatch the latch mechanism 146 allowing anvil half 166b and pusher half 168b to pivot away from anvil half 166a and pusher half 168a. Thus, as shown in FIGS. 35 and 36, collar lever 32 is rotated relative to handle housing 20 within collar lever slot 34 (FIG. 1) until collar lever 32 can be moved distally within longitudinal portion 38 of collar lever slot 34. Thus, as shown in FIG. 36, release notches 102 of release collar 100 fit over release projections 104 in handle housing 22 and allow release collar 100 to move an additional small distance distally. The additional small movement of release collar 100 allows pusher tube 52 to move an additional distance carrying with it catch 158 until catch 158 clears leg portion 152 of latch 148 (FIG. 37).

Figure 38:
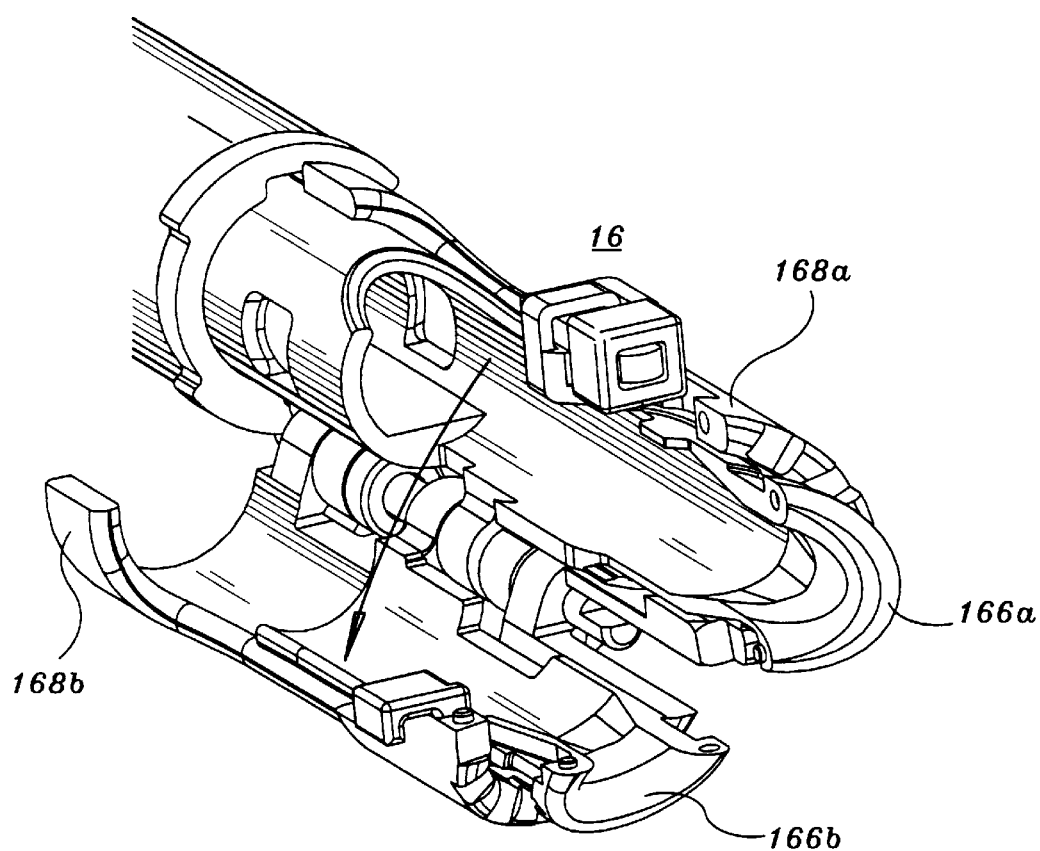
FIG. 38 is a perspective view of the detachable loading unit with halves opened to release the harvested vessel from the detachable loading unit.

In this position, anvil half 166b and pusher half 168b may be pivoted away from anvil half 166a and pusher half 168a in order to release the IMA as shown in FIG. 38. Release of DLU 16 from surgical instrument 10 for installation of a new DLU or reloading of DLU 16 is accomplished by releasing handles 24 against the bias of spring 96 drawing pusher tube 52 proximally out of engagement with pusher 126. Lock slider 26 is moved proximally to draw center rod 40 from within arms 64 and DLU 16 is pulled free of surgical instrument 10.

Figure 39:
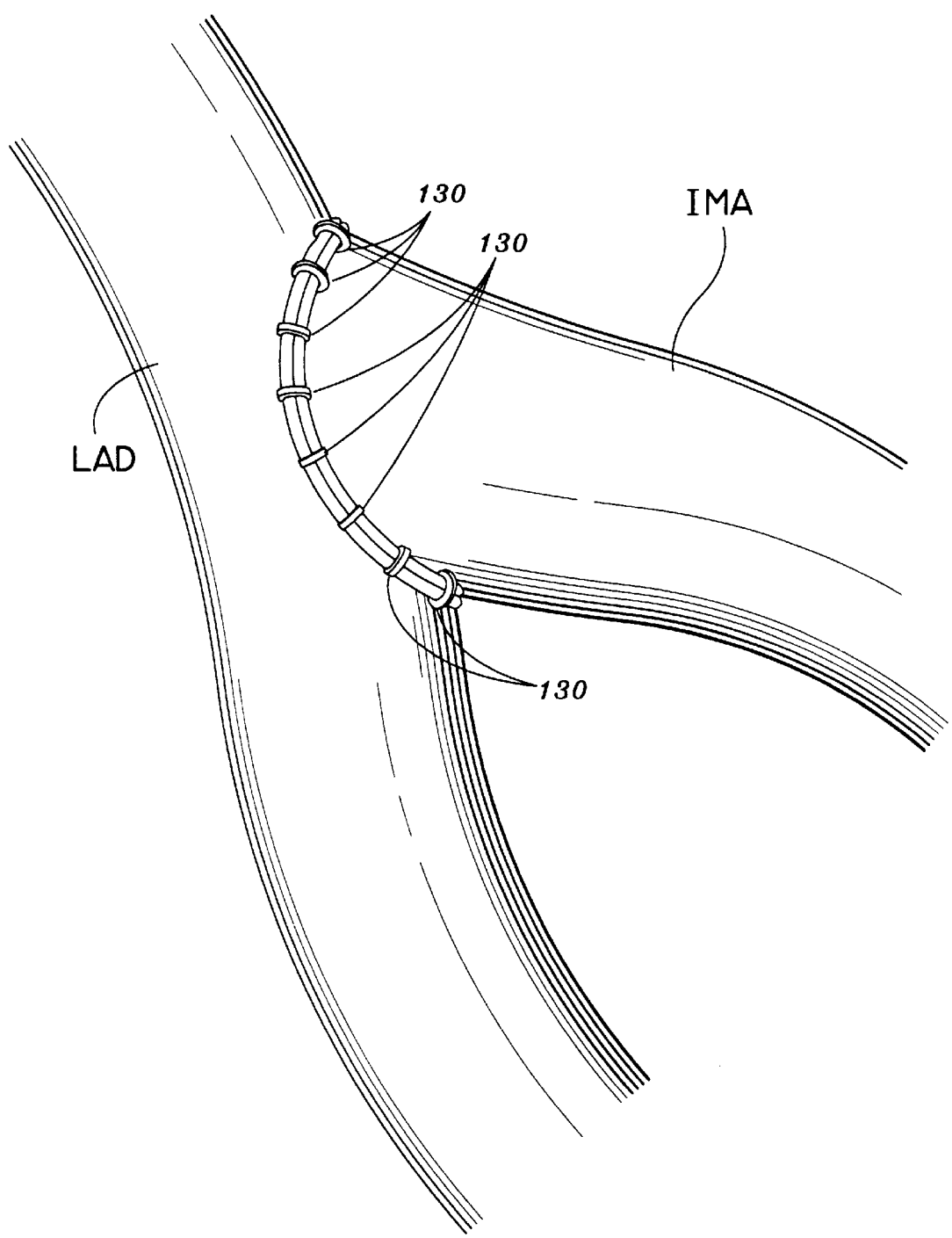
FIG. 39 is a perspective view of the end-to-side anastomosis formed by the surgical instrument and detachable loading unit of FIG. 1.

FIG. 39 illustrates the IMA anastomosed to the LAD by clips 130 utilizing surgical instrument 10 and detachable loading unit 16. The completed graft permits increased blood flow downstream from the inclusion. Any clamps previously provided on the IMA may be removed. If cardiopulmonary bypass is used, it is gradually removed. Alternatively, a clamp used on the coronary artery to restrict blood flow during the operation is removed and normal blood flow is permitted to resume. Surgical instrument 10 and DLU 16 may also have particular use for example in minimally invasive CABG procedures such as thoroscopic procedures for grafting the IMA to the LAD.

It will be understood that various modifications may be made to the embodiment shown here. For example, various orientations of the anvil, pusher and mounted IMA are contemplated to provide end-to-end anastomosis capabilities. Therefore, the above description should not be construed as limiting, but merely as exemplifications of preferred embodiments. Those skilled in the art will envision other modifications within the scope and spirit of the claims appended hereto.

What is claimed is:

1. A detachable loading unit for use with a surgical fastener apparatus comprising:
   a) a generally cylindrical anvil member having structure for releasably engaging a portion of a surgical fastener apparatus;
   b) a plurality of surgical clips circumferentially disposed on the anvil member; and
   c) a pusher coaxially mounted with respect to the anvil member such that the clips are held between a distal end of the anvil and a distal end of the pusher.

2. The loading unit as recited in claim 1, wherein the anvil member and pusher define a passage for receipt of a segment of vascular tissue.

3. The loading unit as recited in claim 1, wherein the pusher is formed of a pair of pusher halves pivotally connected together.

4. The loading unit as recited in claim 3, wherein the anvil member is formed as pair of anvil halves pivotably connected together.

5. The loading unit as recited in claim 4, wherein the pusher halves and the anvil halves pivot about a common axis.

6. The loading unit as recited in claim 4, further comprising a latch mechanism for releasably retaining the anvil halves and pusher halves together.

7. The loading unit as recited in claim 1, further comprising a locking disk positionable about a proximal end of the anvil member and against a proximal end of the pusher member such that the clips are retained between the anvil member and the pusher.

8. The loading unit as recited in claim 1, wherein the pusher includes structure for engagement with corresponding structure on the surgical fastener apparatus.

9. The loading unit as recited in claim 1, wherein distal movement of the pusher relative to the anvil member simultaneously deforms the clips.

10. The loading unit as recited in claim 1, wherein the surgical clips are positioned within longitudinal channels formed in an outer surface of the anvil member.

11. A detachable loading unit for use with a surgical fastener apparatus comprising:
    a) an anvil member releasably engagable with a portion of a surgical apparatus; and
    b) a plurality of surgical clips circumferentially disposed on the anvil member, wherein the anvil member defines a bore for receipt of a section of vascular tissue therein.

12. The loading unit as recited in claim 11, wherein leg portions of the plurality of surgical clips are directed radially outwardly of the bore.

13. The loading unit as recited in claim 11, wherein a first end of the bore is open to a distal end of the anvil member and a second end of the bore forms an exit in the anvil member distal to the proximal end of the anvil member.

14. The loading unit as recited in claim 11, wherein a portion of the anvil member defining the bore is formed as halves pivotally connected together.

15. The loading unit as recited in claim 11, further comprising a pusher coaxially mounted about the anvil, the pusher and the anvil member defining the bore.

16. A detachable loading unit for use with a surgical fastener apparatus comprising:
    a) a fastener support removably engagable with a portion of a surgical fastener apparatus; and
    b) a plurality of surgical clips circumferentially disposed on the fastener support, wherein each clip of the plurality of surgical clips is an atraumatic non-tissue penetrating surgical clip.

17. The loading unit as recited in claim 16, wherein each surgical clip is positioned within a longitudinal channel formed in the fastener support.

18. The loading unit as recited in claim 16, wherein each surgical clip includes at least one leg which is oriented to point substantially radially outward relative to the fastener support.

19. The loading unit as recited in claim 18, wherein each leg terminates in an atraumatic non-tissue penetrating tip.

20. The loading unit as recited in claim 16, wherein the fastener support includes a first camming surface against which the plurality of surgical clips are deformed.

21. The loading unit as recited in claim 20 further comprising a fastener camming member slidably mounted on the fastener support, the fastener camming member including a second camming surface such that movement of the fastener camming member relative to the fastener support deforms the plurality of surgical clips between the first and second camming surfaces.

22. The loading unit as recited in claim 16, wherein the fastener support defines a bore for receipt of a segment of tubular tissue therein.

23. The loading unit as recited in claim 16, wherein the fastener support is formed as halves pivotably connected together.

24. A surgical instrument comprising:
    a) a handle assembly;
    b) an anvil support extending distally from the handle assembly;
    c) an actuator movable with respect to the anvil support; and
    d) a loading unit having:
       i) an anvil removably supported on a distal end of the anvil support;
       ii) a plurality of surgical clips circumferentially disposed about the anvil member; and
       iii) a pusher movable relative to the anvil member and engagable with the actuator, wherein movement of the actuator relative to the anvil support simultaneously deforms the plurality of surgical clips between the anvil member and a distal end of the pusher.

25. The surgical instrument as recited in claim 24, further comprising a slider mechanism movable between a first position remote from the anvil and a second position firmly affixing the anvil to the distal end of the anvil support.

26. The surgical instrument as recited in claim 24, wherein the actuator includes at least one handle movably mounted to the handle assembly.

27. The surgical instrument as recited in claim 26, further comprising a lockout button movably mounted to the housing and movable between a first position blocking movement of the at least one handle and a second position allowing movement of the at least one handle.

28. The surgical instrument as recited in claim 24, wherein the anvil defines a passage for receipt of a blood vessel.

29. The surgical instrument as recited in claim 28, further comprising a latch mechanism on the anvil and actuable from the handle assembly to release the blood vessel from within the passage.

30. A method for anastomosis of first and second tubular tissues comprising:
  a) providing a loading unit having an anvil member defining a passage therethrough for receipt of a first tubular tissue, a plurality of surgical clips having at least one leg with an atraumatic tip positioned on the anvil and a pusher axially movable relative to the anvil to simultaneously deform the plurality of surgical clips;
  b) positioning a first tubular tissue through the passage and everting a first end of the first tubular tissue over a distal end of the anvil and the at least one leg;
  c) inserting the distal end of the anvil and everted first end of first tubular tissue through an opening formed in a second tubular tissue;
  d) engaging the distal end of a surgical instrument with a proximal end of the anvil; and
  e) actuating the surgical instrument to move the pusher distally such that the plurality of surgical clips are crimped about the first and second tubular tissues without piercing the first and second tubular tissues.

* * * * *